(12) United States Patent
Bermudes et al.

(10) Patent No.: US 6,447,784 B1
(45) Date of Patent: Sep. 10, 2002

(54) GENETICALLY MODIFIED TUMOR-TARGETED BACTERIA WITH REDUCED VIRULENCE

(75) Inventors: David Bermudes, Wallingford, CT (US); Kenneth Brooks Low, Guilford, CT (US)

(73) Assignees: Vion Pharmaceuticals, Inc., New Haven, CT (US); Yale University, New Haven, CT (US)

( * ) Notice: Subject to any disclaimer, the term of this patent is extended or adjusted under 35 U.S.C. 154(b) by 0 days.

(21) Appl. No.: 09/149,832

(22) Filed: Sep. 8, 1998

Related U.S. Application Data

(63) Continuation-in-part of application No. 08/926,636, filed on Sep. 10, 1997, now Pat. No. 6,080,849.

(51) Int. Cl.$^7$ .......................... A61K 39/112; C12N 1/20
(52) U.S. Cl. ................. 424/235.1; 424/93.2; 424/93.4; 424/258.1; 435/252.3; 435/879; 435/252.8
(58) Field of Search .......................... 435/252.3, 252.8, 435/879; 536/23.1, 23.7; 514/2, 44; 424/235.1, 258.1, 93.2, 93.4

(56) References Cited

U.S. PATENT DOCUMENTS

| | | | |
|---|---|---|---|
| 4,436,727 A | 3/1984 | Ribi | |
| 5,021,234 A | 6/1991 | Ehrenfeld | |
| 5,344,762 A | 9/1994 | Karapetian | |
| 5,877,159 A | 3/1999 | Powell et al. | |
| 5,997,881 A | 12/1999 | Powell et al. | |
| 6,080,849 A | * 6/2000 | Bermudes et al. | ......... 536/23.7 |

FOREIGN PATENT DOCUMENTS

| | | |
|---|---|---|
| WO | WO 91/06317 | 5/1991 |
| WO | WO 92/11361 | 7/1992 |
| WO | WO 95/02048 | 1/1995 |
| WO | WO 96/11277 | 4/1996 |
| WO | WO 96/34631 | 11/1996 |
| WO | WO 96/40238 | 12/1996 |
| WO | WO97/18837 | * 5/1997 |
| WO | WO 97/18837 | 5/1997 |
| WO | WO 97/19688 | 6/1997 |
| WO | WO 97/25061 | 7/1997 |
| WO | WO 98/33923 | 8/1998 |

OTHER PUBLICATIONS

Adler, 1973, "A Method for Measuring Chemotaxis and Use of the Method to Determine Optimum Conditions for Chemotaxis by *Escherichia coli*", J. Gen. Microbiol. 74:77–91.

Alizadeh et al., 1994, "Apoptosis as a Mechanism of Cytolysis of Tumor Cells by a Pathogenic Free–Living Amoeba", Infect. Immun. 62:1298–1303.

Bagshawe, 1995, "Antibody–Directed Enzyme Prodrug Therapy: A Review", Drug Dev. Res. 34:220–230.

Barry et al., 1995, "Protection Against Mycoplasma Infection Using Expression–Library Immunization", Nature 377:632–635.

Barth and Morton, 1995, "The Role of Adjuvant Therapy in Melanoma Management", Cancer 75 (Suppl.):726–734.

Berggren, 1995, "Recombinant Salmonella as an Oral HIV Vaccine", NIH Project No. 5 K08 AI01248–02.

Bone, 1993, "Gram–Negative Sepsis: A Dilemma of Modern Medicine", Clin. Microbiol. Rev. 6:57–68.

Bonnekoh et al., 1995, "Inhibition of Melanoma Growth by Adenoviral–Mediated HSV Thymidine Kinase Gene Transfer in vivo", J. Invest Derm. 104:313–317.

Carey et al., "Clostridial Oncolysis in Man", Eur. J. Cancer 3:37–46.

Carrier et al., 1992, "Expression of Human IL–1β in *Salmonella typhimurium*; a Model System for the Delivery of Recombinant Therapeutic Proteins in vivo", J. Immunol. 148:1176–1181.

Carswell et al., 1975, "An Endotoxin–Induced Serum Factor that Causes Necrosis of Tumors", Proc. Natl. Acad. Sci. USA 72:3666–3670.

Chabalgoity et al., 1996, "A *Salmonella typhimurium* htrA Live Vaccine Expressing Multiple Copies of a Peptide Comprising Amimo Acids 8–23 of Herpes Simplex Virus Glycoprotein D as a Genetic Fusion to Tetanus Toxin Fragment C Protects Mice from Herpes Simplex Virus Infection", Mol. Microbiol. 19:791–801.

Christ et al., 1995, "E5531, a Pure Endotoxin Antagonist of High Potency", Science 268:80–83.

Clements, 1995, "Attenuated Salmonella as Vaccine Vectors", NIH Project No. 5 R01 AI 28835–06.

Clementz et al., 1997, "Function of the *Escherichia coli* msbB Gene, a Multicopy Suppressor of htrB Knockouts, in the Acylation of Lipid A", J. Biol. Chem. 272(16):10353–10360.

Cunningham et al., 1992, "Actin–Binding Protein Requirement for Cortical Stability and Efficient Locomotion", Science 255:325–327.

Curtiss, 1995, "Biological Containment of Live Bacterial Vaccines", NIH Project No. 1 R41 AI38599–01.

Curtiss, 1994, "Avirulent Salmonella Host–Vector Vaccine Systems", NIH Project No. 1 R41 AI36585–01.

(List continued on next page.)

Primary Examiner—Phuong T. Bui
(74) Attorney, Agent, or Firm—Pennie & Edmonds LLP

(57) ABSTRACT

The present invention is directed to mutant Salmonella sp. having a genetically modified msbB gene in which the mutant Salmonella is capable of targeting solid tumors. The invention is also directed to Salmonella sp. containing a genetically modified msbB gene as well as an genetic modification in a biosynthetic pathway gene such as the purI gene. The present invention further relates to the therapeutic use of the mutant Salmonella for growth inhibition and/or reduction in volume of solid tumors.

22 Claims, 16 Drawing Sheets

OTHER PUBLICATIONS

Figures 3A, 3B, 3C:
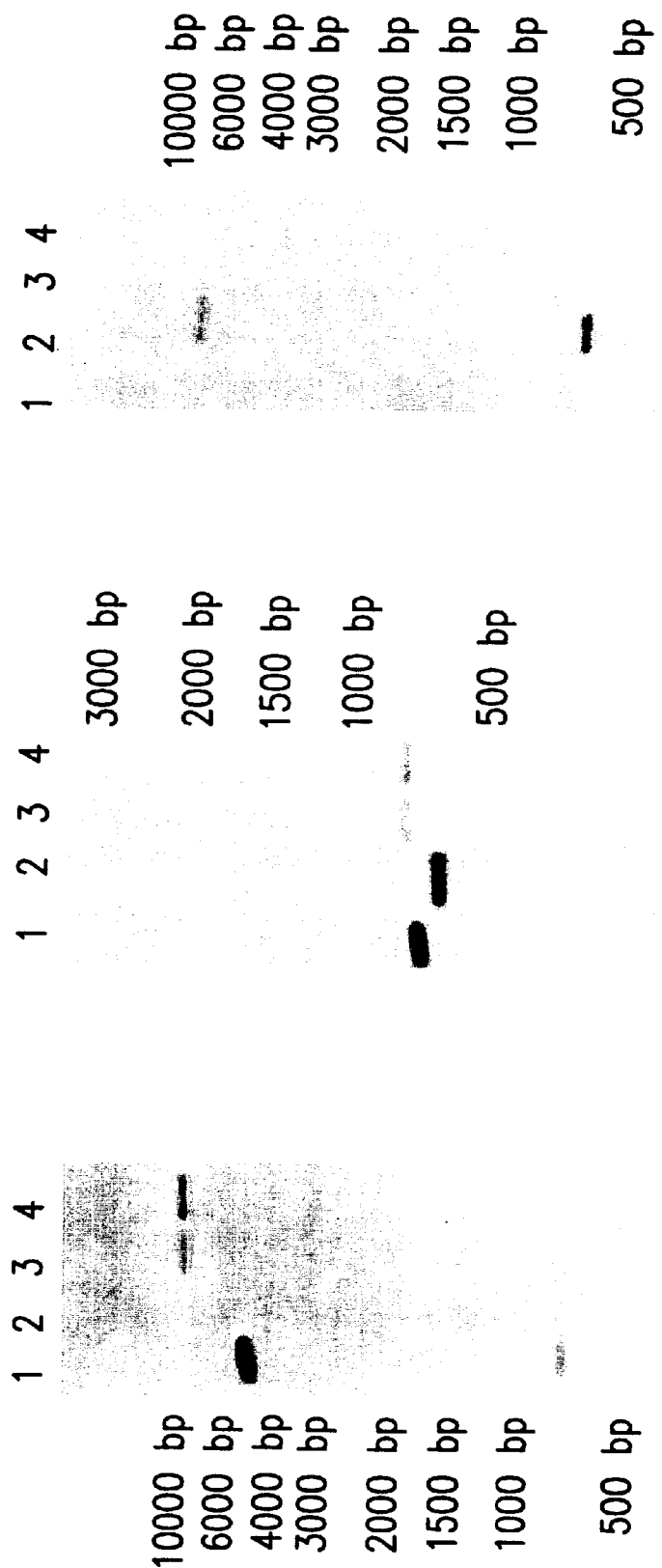

Eisenstadt, 1987, "Analysis of Mutagenesis", from *Escherichia coli and Salmonella typhimurium, Cellular and Molecular Biology*, Neidhardt et al. (ed.), pp. 1016–1033.

Eisenstein et al., 1995, "Immunotherapy of a Plasmacytoma with Attenuated Salmonella", Med. Oncol. 12:103–108.

Engelbart and Gericke, 1963, "Oncolysis by Clostridia. V. Transplanted Tumors of the Hamster", Cancer Res. 24:239–243.

Falkow, 1991, "Bacterial Entry into Eukaryotic Cells", Cell 65:1099–1102.

Fox et al., 1996, "Anaerobic Bacteria as a Delivery System for Cancer Gene Therapy: in vitro Activation of 5–Fluorocytosine by Genetically Engineered Clostridia", Gene Therapy 3:173–178.

Friberg, 1993, "BCG in the Treatment of Superficial Cancer of the Bladder: A Review", Med. Oncol. Tumor Pharmacother. 10:31–36.

Galan, 1995, "Novel Salmonella Antigen Delivery Vectors", NIH Project No. 5 R01 AI36520–02.

Gericke and Engelbart, 1963, "Oncolysis by Clostridia. II. Experiments on a Tumor Spectrum with a Variety of Clostridia in Combination with Heavy Metal", Cancer Res. 24:217–221.

Gulig, 1994, "Salmonella typhimurium Virulence Plasmid", NIH Project No. 5 R29 AI28421–05.

Hall et al., 1994, "Induced Regression of Bovine Papillomas by Intralesional Immunotherapy", Therapeutic Immunol. 1:319–324.

Han et al., 1967, "Salmonellosis in Disseminated Malignant Diseases", New Eng. J. Med. 276:1045–1052.

Jain, 1994, "Barriers to Drug Delivery in Solid Tumors", Sci. American 271:58–65.

Jones et al., 1992, "Invasion by *Salmonella typhimurium* is Affected by the Direction of Flageller Rotation", Infect. Immun. 60:2475–2480.

Karow and Georgopoulos, 1992, "Isolation and Characterization of the *Escherichia coli* msbB Gene, a Multicopy Suppressor of Null Mutations in the High–Temperature Requirement Gene htrB", J. Bacteriol. 174:702–710.

Klimpel et al., 1990, "Bacteria–Infected Fibroblasts have Enhanced Susceptibility to the Cytotoxic Action of Tumor Necrosis Factor", J. Immunol. 145:711–717.

Lee et al., 1992, "Identification of a *Salmonella typhimurium* Invastion Locus by Selection for Hyperinvasive Mutants", Proc. Natl. Acad. Sci. USA 89:1847–1851.

Lemmon et al., 1994, "Anaerobic Bacteria as a Gene Delivery System to Tumors", Proc. Am. Assn. Cancer Res. 35:374 (Abstract 2231).

Lemmon et al., 1997, "Anaerobic Bacteria as a Gene Delivery System that is Controlled by the Tumor Microenvironment", Gene Therapy, 4:791–796.

Levine, 1995, "Recombinant and Live Oral *Salmonella typhi* Vaccines", NIH Project No. 5 R01 AI29471–06.

Loppnow et al., 1990, "Cytokine Induction by Lipopolysaccharide (LPS) Corresponds to Lethal Toxicity and is Inhibited by Nontoxic *Rhodobacter capsulatus* LPS", Infect Immun. 58:3743–3750.

Lytvyn et al., 1992, "Comparison of the Thymidine Kinase Genes from Three Entomopoxviruses", J. Gen. Virol. 73:3235–3240.

Macnab, 1992, "Genetics and Biogenesis of Bacterial Flagella", Ann. Rev. Genet. 26:131–158.

Mahan et al., 1993, "Selection of Bacterial Virulence Genes that are Specifically Induced in Host Tissues", Science 259:686–688.

McLaughlin et al., 1979, "Synergistic Activity of Components of Mycobacteria and Mutant Salmonella in Causing Regression of Line–10 Tumors in Guinea Pigs", Cancer Res. 39:1766–1771.

Michalek, 1994, "Genetically Engineered Oral Vaccines and Caries Immunity", Abstract, NIH Project No. 5 R01 DE09081–05.

Miller et al., 1989, "A Two–Component Regulatory System (phoP phoQ) Controls *Salmonella typhimurium* Virulence", Proc. Natl. Acad. Sci. USA 86:5054–5058.

Miller, 1995, "Entry into Eukaryotic Cells by Salmonella and Yersinia", NIH Project No. 5 K04 AI01230–02.

Miller et al., 1992, "An Unusual pagC::TnphoA Mutation Leads to an Invasion– and Virulence–Defective Phenotype in Salmonellae", Infect. Immun. 60:3763–3770.

Minton et al., 1995, "Chemotherapeutic Tumor Targeting Using Clostridial Spores", FEMS Micro. Rev. 17:357–364.

Möse and Möse, 1963, "Oncolysis by Clostridia. I. Activity of *Clostridium butyricum* (M–55) and Other Nonpathogenic Clostridia Against the Ehrlich Carcinoma", Cancer Res. 24:212–216.

Mullen et al., 1992, "Transfer of the Bacterial Gene for Cytosine Deaminase to Mammalian Cells Confers Lethal Sensitivity to 5–Fluorocytosine: a Negative Selection System", Proc. Natl. Acad. Sci USA 89:33–37.

Nauts et al., 1953, "A Review of the Influence of Bacterial Infection and of Bacterial Products (Coley's Toxins) on Malignant Tumors in Man", Acta Medica Scandinavica 145 (Suppl. 276):1–105.

Pan et al., 1995, "A Recombinant *Listeria monocytogenes* Vaccine Expressing a Model Tumor Antigen Protects Mice Against Lethal Tumor Cell Challenge and Causes Regression of Established Tumors", Nature Medicine 1:471–477.

Parker et al., 1947, "Effect of Histolyticus Infection and Toxin on Transplantable Mouse Tumors", Proc. Soc. Exp. Biol. Med. 16124:461–467.

Pawelek et al., 1995, "Macrophage Characteristics of Metastatic Melanoma", J. Invest. Dermatol. 104:605 (Abstract 304).

Pawelek et al., 1997, "Tumor–targeted Salmonella as a Novel Anti–cancer Vector", Cancer Res., 57:4537–4544.

Pidherney et al., 1993, "In vitro and in vivo Tumoricidal Properties of a Pathogenic Free–Living Amoeba", Cancer Letters 72:91–98.

Pugsley, 1988, "Protein Secretion Across the Outer Membrane of Gram–Negative Bacteria" In: *Protein Transfer and Organelle Biogenesis*, D and Robbins (eds.), Academic Press, Inc., Harcourt Brace Jovanovich, Publishers, San Diego, pp. 607–652.

Raue and Cashel, 1975, "Regulation of RNA Synthesis in *Escherichia coli*", Biochimica et Biophysica Acta 383:290–304.

Reinhard et al., 1950, "Chemotherapy of Malignant Neoplastic Diseases", JAMA 142:383–390.

Saltzman et al., 1996, "Attenuated *Salmonella typhimurium* Containing Interleukin-2 Decreases MC–38 Hepatic Metastases: a Novel Anti–Tumor Agent", Cancer Biotherapy and Radiopharmaceuticals 11:145–153.

Schafer et al., 1992, "Induction of a Cellular Immune Response to a Foreign Antigen by a Recombinant *Listeria monocytogenes* Vaccine", J. Immunol. 149:53–59.

Schlechte and Elbe, 1988, "Recombinant Plasmid DNA Variation of *Clostridium oncolyticum*—Model Experiments of Cancerostatic Gene Transfer", Zbl. Bakt. Hyg. A 268:347–356.

Schlechte et al., 1982, "Chemotherapy for Tumors Using Clostridial Oncolysis, Antibiotics and Cyclophosphamide: Model Trial on the UVT 15264 Tumor", Arch. Geschwulstforsch. 52:41–48.

Shaw et al., 1991, "The Human Dioxin–Inducible NAD(P)H: Quinone Oxidoreductase cDNA–Encoded Protein Expressed in COS–1 Cells is Identical to Diaphorase 4", Eur. J. Biochem. 195:171–176.

Sizemore et al., 1995, "Attenuated Shigella as a DNA Delivery Vehicle for DNA–Mediated Immunization", Science 270:299–302.

Slauch et al., 1994, "In vivo Expression Technology for Selection of Bacterial Genes Specifically Induced in Host Tissues", Meth. Enzymol. 235:481–492.

Somerville et al., 1996, "A Novel *Escherichia coli* Lipid A Mutant that Produces an Antiinflammatory Lipopolysaccharide", J. Clin. Invest. 97:359–365.

Sosnowski et al., 1994, "Complications of Bacillus Calmette–Guerin (BCG) Immunotherapy in Superficial Bladder Cancer", Comp. Ther. 20:695–701.

Su et al., 1992, "Extracellular Export of Shiga Toxin B–Subunit/Haemolysin A (C–terminus) Fusion Protein Expressed in *Salmonella typhimurium* aroA–Mutant and Stimulation of B–Subunit Specific Antibody Responses in Mice", Microbial Pathogenesis 13:465–476.

Sunshine et al., 1997, "Mutation of the htrB Gene in Virulent *Salmonella typhimurium* Strain by Intergeneric Transduction: Strain Construction and Phenotypic Characterization", J. Bacteriol., 179(17):5521–5533.

Takayma et al., 1989, "Diphosphoryl Lipid from *Rhodopseudomonas sphaeroides* ATCC 17023 Blocks Induction of Cachectin in Macrophages by Lipopolysaccharide", Infect. Immun. 57:1336–1338.

Thiele et al., 1963, "Oncolysis by Clostridia. III. Effects of Clostridia and Chemotherapeutic Agents on Rodent Tumors", Cancer Res. 24:222–232.

Thiele et al., 1963, "Oncolysis by Clostridia. IV. Effect of Nonpathogenic Clostridial Spores in Normal and Pathological Tissues", Cancer Res. 24:234–238.

Tuomanen, 1993, "Subversion of Leukocyte Adhesion Systems by Respiratory Pathogens", Am. Soc. Microbiol. 59:292–296.

Vinopal, 1987, "Selectable Phenotypes", from *Escherichia coli and Salmonella typhimurium, Cellular and Molecular Biology*, Neidhardt et al. (ed.), pp. 990–1015.

Wolfe et al., 1971, "Salmonellosis in Patients with Neoplastic Disease", Arch. Intern. Med. 128:547–554.

Anderson et al., 1996, "Development of attenuated Salmonella strains that express heterologous antigens", Methods in Molecular Medicine: Vaccine protocols, ed. Robinson A, Farrar G, Wiblin C., Humana Press New Jersey, pp. 47–62.

Engel et al., 1992, "Murein–metabolizing enzymes from *Escherichia coli*: existence of a second lytic transglycosylase", J. Bacteriol. 174:6394–6403.

Kelley et al., 1993, "The firA gene o E. coli encodes UDP–3–O–(R–3–hydroxymyristoyl)–glucosamine –acetyltransferase", J. Biol. Chem. 268:19866–19874.

Lindgren et al., 1996, "Macrophage killing is an essential virulence mechanism of *Salmonella typhimurium*", PNAS, 93(9) 4197–4201.

Sizemore et al., 1997, "Interaction– of *Salmonella typhi* strains with cultured human monocyte–derived macrophages", Infect. Immunity 65:309–312.

Khan et al., 1998, "A lethal role for lipid A in Salmonella Infections", Mol. Microbiol. 29(2):571–579.

* cited by examiner

GATCAACCAGCAAGCCGTTAACCCTCTGACAGCAAAATTGCCCGGCACGGAAGGTCTGACGGGGTCAGATGCTCGTGAATACCTGGCACA 90
GGTGAAAGAGGTTCTGCCCGCCAACTGCCGCTTCGATTAACAAATGCGCTGACAGAGCCGGTACGCGATGTGTGCCGGCTTTTTGTTTGTG 180

M E T K K N N S E
TGAGACGGCAGAGATCGCTACACTATTCACAATTCCTTTTCCGTCAGCAGACCTGAAACCAAAAAATAATAGTGAG 270

Y I P E F K S F R Y P Q Y W G A W L G A A A M A G I A L T
TATATCCCTGAATTCGAAAAATCCTTTCGCTATCCACAGTATTGGGGCGCCTGGTTGGGCGCGGCCAATGCGGGGATCGCATTAACA 360

P A S F R D P L L A T L G R F A G R L G K S S R R A L I N
CCGGCATCATTCCGGCACCCTTTGCTCGGGACGCGCTGGGGCGTTTGCCGGACGGCTGGGGAAGAGTTCTCGTCCGGGCGCTAATTAAT 450

L S L C F P Q R S E A E R E A I V D E M F A T A P Q A M A M
CTGTCGTTGTGCTTTCCGCAGCGTAGCGAAGCTGAGCGCGAACGCCATTGTCGATGAGATGTTCGCCACCGCCCACCAGGCCAATGCCGATG 540

M A E L A M R G P K K I Q Q R V D W E G L E I I E E M R R N
ATGGCTGAGTTGGCGATGCGCGGTCCGAAGAAAATTCAACACGCGTGTTGACTGGGAAGGTCTGGAGATTATCGAGGAGATGCGTCGTAAC 630

D E K V I F L V P H G W G V D I P A M L M A S Q G Q K M A A
GACGAAAAAGTCATTTTTCTCGTACCCCATGGCTGGGGCGTCGACATTCCAGCATGCTGATGGCCTCTCAGGGGCAAAAATGGCCGCCG 720

M F H N Q G N P V F D Y I W N T V R R F G G R L H A R N D
ATGTTTCATAATCAGGGTAATCCGGTTTTTGACTATATCTGGAACACAGTGCGTCGGCGTTTCGGCGGACGTTTGCATGCGCGTAATGAC 810

G I K P F I Q S V R Q G Y W G Y Y L P D Q D H G P E H S E F
GGGATTAAACCCTTTATTCAGTCTGTCGTTCAGGGCTACTGGGGTTACTACCTGCCGGACCAGGATCACGGCCCGGAGCATAGTGAATTC 900

FIG.1A

```
V  D  F  F  A  T  Y  K  A  T  L  P  A  I  G  R  L  M  K  V  C  R  A  R  V  I  P  L  F  P
GTTGATTTCTTTTGCGACATACAAAGCGACGCTGCCTGCAATTGGTCGGCTGATGAAAGTGTGCCGGCCACGGCTGATACCCCTTTTCCCG    990

V  Y  N  G  K  T  H  R  L  T  I  Q  I  R  P  P  M  D  D  L  L  T  A  D  D  H  T  I  A  R
GTGTATAATGGTAAAACGCATCGCCTGACTATCCAGATTCGCCCGCCAATGGACGATCTGCTCACGGCTGACGACCACACTATCGCCAGA    1080

R  M  N  E  E  V  E  I  F  V  G  P  H  P  E  Q  Y  T  W  I  L  K  L  L  K  T  R  K  P  G
CGGATGAACGAAGAGGTCGAAATTTTTGTCGGCCCGCATCCCGAACAGTACACCTGGATCCTGAAGCTGCTCAAAACCCGCAAGCCAGGC    1170

E  I  Q  P  Y  K  R  K  D  L  Y  P  I  K
GAGATTCAGCCGTATAAGCGTAAAGATCTTTATCCCATCAAATAAATAAAGCCTCTCGTAAGAGAGCTTTATGCTGCAAACCCTCTAC    1260

TACCTGATGAACAGGGCGTGGGGGAGTTTTACTCAACGGTCAAATACGGGTGGTATTGGTTGAACGACGGTGCTCATGACATCGCCCTG    1350

GGTCACGATAACCAGGTCCCCGGAAACCAGATACCCTTTATCCGCAGCAGATTAACAGTTCATGTCCCGGACAACGCCATCAGCGCC    1440

GCTATCAAAATGCACCGGCGTTACTCCCGATAGAGCGCGTCAGGTTCAGCGTCGTTGATGGCCGGTAACGCCTTCAGATGGTTGCCGCATA    1530

GGAGCTGATACGGGAAGTCATTAGCGCGGTACGACCGGATTCCGTCGAACTGCACGTCGAGACGGTGTTTAGACACATTGATGCTGGGGATTTTTTCTGC    1620

CATCCCAGACACATGGCTTCTTCAACGTTGTCGAACGGTTTCAGAAGGATACTGACCGGCTGCGGTTTCGGCAGACAGCATAACCGCATCCGTCC    1710

GCCCAGGCAGACGCCCCCATTGCGGCAACGGTTCAGAAGGATACTGACCGGCTGCGGTTTCGGCAGACAGCATAACCGCATCCGTGCC    1800

ATCCAGGACGGCGTTCGCCACGTCCATCACTTCCCGCACGGTCGGCATCGGTTGGTGATCATCGACTCCATCATTTGCGTTGCGGTGAT    1890

GACTGCGCGGTTTAGCTGACGCGCACGCGGAATCAGCGGCTTCTGGATACCAACCAGTCCGGATCGCCGATTTCAACGCCCAGATCGCC    1980

ACGTGCGACCATCACAACGTCAGAGGCCAGAATGATATC    2019
```

FIG.1B

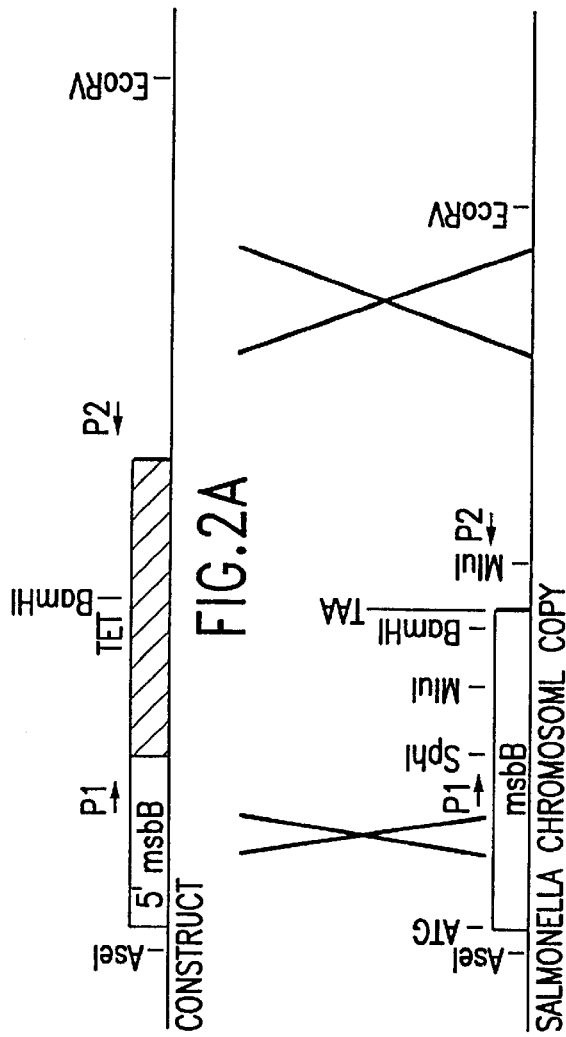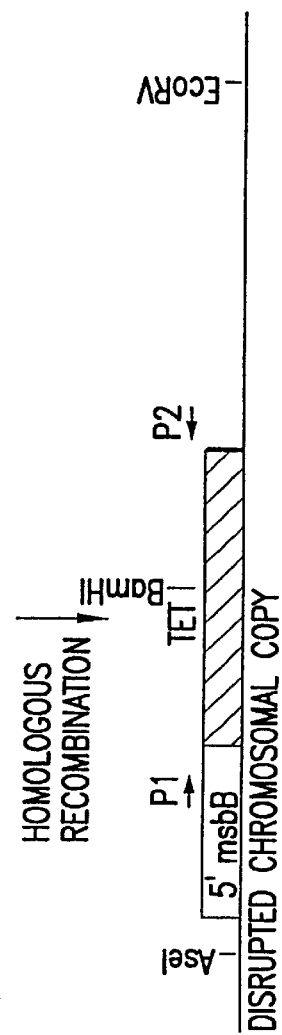

GENETICALLY MODIFIED TUMOR-TARGETED BACTERIA WITH REDUCED VIRULENCE

This application is a continuation-in-part of application Ser. No. 08/926,636, filed Sep. 10, 1997, now U.S. Pat. No. 6,080,849, the entire disclosure of which is incorporated by reference herein in its entirety.

1. FIELD OF THE INVENTION

The present invention is concerned with the isolation of a gene of Salmonella which, when genetically disrupted, reduces both virulence and septic shock caused by this organism and increases sensitivity to agents which promote eradication of the bacteria, e.g., chelating agents. The nucleotide sequence of this gene and the means for its genetic disruption are provided, and examples of the use of tumor-targeted bacteria which possess a disruption in this gene to inhibit growth of cancers, including, but not limited to, melanoma, colon cancer, and other solid tumors are described. The present invention also provides for the genetic disruption of this gene in combination with disruption of an auxotrophic gene.

2. BACKGROUND OF THE INVENTION

Citation or identification of any reference in Section 2, or any section of this application shall not be construed as an admission that such reference is available as prior art to the present invention.

A major problem in the chemotherapy of solid tumor cancers is delivery of therapeutic agents, such as drugs, in sufficient concentrations to eradicate tumor cells while at the same time minimizing damage to normal cells. Thus, studies in many laboratories are directed toward the design of biological delivery systems, such as antibodies, cytokines, and viruses for targeted delivery of drugs, pro-drug converting enzymes, and/or genes into tumor cells. Houghton and Colt, 1993, New Perspectives in Cancer Diagnosis and Management 1: 65–70; de Palazzo, et al., 1992a, Cell. Immunol. 142:338–347; de Palazzo et al., 1992b, Cancer Res. 52: 5713–5719; Weiner, et al., 1993a, J. Immunotherapy 13:110–116; Weiner et al., 1993b, J. Immunol. 151:2877–2886; Adams et al., 1993, Cancer Res. 53:4026–4034; Fanger et al., 1990, FASEB J. 4:2846–2849; Fanger et al., 1991, Immunol. Today 12:51–54; Segal, et al., 1991, Ann N.Y. Acad. Sci. 636:288–294; Segal et al., 1992, Immunobiology 185:390–402; Wunderlich et al., 1992; Intl. J. Clin. Lab. Res. 22:17–20; George et al., 1994, J. Immunol. 152:1802–1811; Huston et al., 1993, Intl. Rev. Immunol. 10:195–217; Stafford et al., 1993, Cancer Res. 53:4026–4034; Haber et al., 1992, Ann. N.Y. Acad. Sci. 667:365–381; Haber, 1992, Ann. N.Y. Acad. Sci. 667: 365–381; Feloner and Rhodes, 1991, Nature 349:351–352; Sarver and Rossi, 1993, AIDS Research & Human Retroviruses 9:483–487; Levine and Friedmann, 1993, Am. J. Dis. Child 147:1167–1176; Friedmann, 1993, Mol. Genetic Med. 3:1–32; Gilboa and Smith, 1994, Trends in Genetics 10:139–144; Saito et al., 1994, Cancer Res. 54:3516–3520; Li et al., 1994, Blood 83:3403–3408; Vieweg et al., 1994, Cancer Res. 54:1760–1765; Lin et al., 1994, Science 265:666–669; Lu et al., 1994, Human Gene Therapy 5:203–208; Gansbacher et al., 1992, Blood 80:2817–2825; Gastl et al., 1992, Cancer Res. 52:6229–6236.

2.1 BACTERIAL INFECTIONS AND CANCER

Regarding bacteria and cancer, an historical review reveals a number of clinical observations in which cancers were reported to regress in patients with bacterial infections. Nauts et al., 1953, Acta Medica. Scandinavica 145:1–102, (Suppl. 276) state:

> The treatment of cancer by injections of bacterial products is based on the fact that for over two hundred years neoplasms have been observed to regress following acute infections, principally streptococcal. If these cases were not too far advanced and the infections were of sufficient severity or duration, the tumors completely disappeared and the patients remained free from recurrence.

Shear, 1950, J. A.M.A. 142:383–390 (Shear), observed that 75 percent of the spontaneous remissions in untreated leukemia in the Children's Hospital in Boston occurred following an acute episode of bacterial infection. Shear questioned:

> Are pathogenic and non-pathogenic organisms one of Nature's controls of microscopic foci of malignant disease, and in making progress in the control of infectious diseases, are we removing one of Nature's controls of cancer?

Subsequent evidence from a number of research laboratories indicated that at least some of the anti-cancer effects are mediated through stimulation of the host immune system, resulting in enhanced immuno-rejection of the cancer cells. For example, release of the lipopolysaccharide (LPS) endotoxin by gram-negative bacteria such as Salmonella triggers release of tumor necrosis factor, TNF, by cells of the host immune system, such as macrophages, Christ et al., 1995, Science 268:80–83. Elevated TNF levels in turn initiate a cascade of cytokine-mediated reactions which culminate in the death of tumor cells. In this regard, Carswell et al., 1975, Proc. Natl. Acad. Sci. USA 72:3666–3669, demonstrated that mice injected with bacillus Calmette-Guerin (BCG) have increased serum levels of TNF and that TNF-positive serum caused necrosis of the sarcoma Meth A and other transplanted tumors in mice. Further, Klimpel et al., 1990, J. Immunol. 145:711–717, showed that fibroblasts infected in vitro with Shigella or Salmonella had increased susceptibility to TNF.

As a result of such observations as described above, immunization of cancer patients with BCG injections is currently utilized in some cancer therapy protocols. See Sosnowski, 1994, Compr. Ther. 20:695–701; Barth and Morton, 1995, Cancer 75 (Suppl. 2):726–734; Friberg, 1993, Med. Oncol. Tumor. Pharmacother. 10:31–36 for reviews of BCG therapy.

2.2 PARASITES AND CANCER CELLS

Although the natural biospecificity and evolutionary adaptability of parasites has been recognized for some time and the use of their specialized systems as models for new therapeutic procedures has been suggested, there are few reports of, or proposals for, the actual use of parasites as vectors.

Lee et al., 1992, Proc. Natl. Acad. Sci. USA 89:1847–1851 (Lee et al.) and Jones et al., 1992, Infect. Immun. 60:2475–2480 (Jones et al.) isolated mutants of *Salmonella typhimurium* that were able to invade HEp-2 (human epidermoid carcinoma) cells in vitro in significantly greater numbers than the wild type strain. The "hyperinvasive" mutants were isolated under conditions of aerobic growth of the bacteria that normally repress the ability of wild type strains to invade HEp-2 animal cells. However, Lee et al. and Jones et al. did not suggest the use of such mutants as therapeutic vectors, nor did they suggest the isolation of tumor-specific bacteria by selecting for mutants that show infection preference for melanoma or other cancers over normal cells of the body. Without tumor-specificity or other forms of attenuation, such hyperinvasive *Salmonella typhimurium* as described by Lee et al. and Jones et al. would likely be pan-invasive, causing wide-spread infection in the cancer patient.

2.3 TUMOR-TARGETED BACTERIA

Genetically engineered Salmonella have been demonstrated to be capable of tumor targeting, possess anti-tumor activity and are useful in delivering effector genes such as the herpes simplex thymidine kinase (HSV TK) to solid tumors (Pawelek et al., WO 96/40238). Two significant considerations for the in vivo use of bacteria are their virulence and ability to induce tumor necrosis factor α (TNFα)-mediated septic shock. As TNFα-mediated septic shock is among the primary concerns associated with bacteria, modifications which reduce this form of an immune response would be useful because TNFα levels would not become toxic, and a more effective concentration and/or duration of the therapeutic vector could be used.

2.4 MODIFIED BACTERIAL LIPID A

Modifications to the lipid composition of tumor-targeted bacteria which alter the immune response as a result of decreased induction of TNFα production were suggested by Pawelek et al. (Pawelek et al., WO 96/40238). Pawelek et al. provided methods for isolation of genes from Rhodobacter responsible for monophosphoryl lipid A (MLA) production. MLA acts as an antagonist to septic shock. Pawelek et al. also suggested the use of genetic modifications in the lipid A biosynthetic pathway, including the mutation firA, which codes for the third enzyme UDP-3-O (R-30 hydroxylmyristoly)-glucosamine N-acyltransferase in lipid A biosynthesis (Kelley et al., 1993, J. Biol. Chem. 268: 19866–19874). Pawelek et al. showed that mutations in the firA gene induce lower levels of TNFα. However, these authors did not suggest enzymes which modify the myristate portion of the lipid A molecule. Furthermore, Pawelek et al. did not suggest that modifications to the lipid content of bacteria would alter their sensitivity to certain agents, such as chelating agents.

In *Escherichia coli*, the gene msbB (mlt) which is responsible for the terminal myristalization of lipid A has been identified (Engel, et al., 1992, J. Bacteriol. 174:6394–6403; Karow and Georgopoulos 1992, J. Bacteriol. 174: 702–710; Somerville et al., 1996, J. Clin. Invest. 97: 359–365). Genetic disruption of this gene results in a stable non-conditional mutation which lowers TNFα induction (Somerville et al., 1996, J. Clin. Invest. 97: 359–365). These references, however, do not suggest that disruption of the msbB gene in tumor-targeted Salmonella vectors would result in bacteria which are less virulent and more sensitive to chelating agents.

The problems associated with the use of bacteria as gene delivery vectors center on the general ability of bacteria to directly kill normal mammalian cells as well as their ability to overstimulate the immune system via TNFα which can have toxic consequences for the host (Bone, 1992 JAMA 268: 3452–3455; Dinarello et al., 1993 JAMA 269: 1829–1835). In addition to these factors, resistance to antibiotics can severely complicate coping with the presence of bacteria within the human body (Tschape, 1996, D T W Dtsch Tierarztl Wochenschr 1996 103:273–7; Ramos et al., 1996, Enferm Infec. Microbiol. Clin. 14: 345–51).

Hone and Powell, WO97/18837 ("Hone and Powell"), disclose methods to produce gram-negative bacteria having non-pyrogenic Lipid A or LPS. Although Hone and Powell broadly asserts that conditional mutations in a large number of genes including msbB, kdsA, kdsB, kdtA, and htrB, etc. can be introduced into a broad variety of gram-negative bacteria including *E. coli*, Shigella sp., Salmonella sp., etc., the only mutation exemplified is an htrB mutation introduced into *E. coli*. Further, although Hone and Powell propose the therapeutic use of non-pyrogenic Salmonella with a mutation in the msbB gene, there is no enabling description of how to accomplish such use. Moreover, Hone and Powell propose using non-pyrogenic bacteria only for vaccine purposes.

The objective of a vaccine vector is significantly different from the presently claimed tumor-targeted vectors. Thus, vaccine vectors have requirements quite different from tumor-targeted vectors. Vaccine vectors are intended to elicit an immune response. A preferred live bacterial vaccine must be immunogenic so that it elicits protective immunity; however, the vaccine must not be capable of excessive growth in vivo which might result in adverse reactions. According to the teachings of Hone and Powell, a suitable bacterial vaccine vector is temperature sensitive having minimal replicative ability at normal physiological ranges of body temperature.

In contrast, preferred tumor-targeted parasitic vectors, such as but not limited to Salmonella, are safely tolerated by the normal tissues of the body such that pathogenesis is limited, yet the vectors target to tumors and freely replicate within them. Thus, vaccine vectors which replicate minimally at normal body temperatures, would not be suitable for use as tumor-targeted vectors.

The preferred properties of tumor-specific Salmonella strains include 1) serum resistance, allowing the parasite to pass through the vasculature and lymphatic system in the process of seeking tumors, 2) facultative anaerobiasis, i.e., ability to grow under anaerobic or aerobic conditions allowing amplification in large necrotic tumors which are hypoxic as well as small metastatic tumors which may be more aerobic, 3) susceptibility to the host's defensive capabilities, limiting replication in normal tissues but not within tumors where the host defensive capabilities may be impaired, 4) attenuation of virulence, whereby susceptibility to the host defenses may be increased, and the parasite is tolerated by the host, but does not limit intratumoral replication, 5) invasive capacity towards tumor cells, aiding in tumor targeting and anti-tumor activity, 6) motility, aiding in permeation throughout the tumor, 7) antibiotic sensitivity for control during treatment and for post treatment elimination (e.g., sensitivity to ampicillin, chloramphenicol, gentamicin, ciprofloxacin), and lacking antibiotic resistance markers such as those used in strain construction, and 8) low reversion rates of phenotypes aiding in the safety to the recipient individual.

3. SUMMARY OF THE INVENTION

The present invention provides a means to enhance the safety of tumor-targeted bacteria, for example, by genetic modification of the lipid A molecule. The modified tumor-targeted bacteria of the present invention induce TNFα less than the wild type bacteria and have reduced ability to directly kill normal mammalian cells or cause systemic disease compared to the wild type strain. The modified tumor-targeted bacteria of the present invention have increased therapeutic efficacy, i.e., more effective dosages of bacteria can be used and for extended time periods due to the lower toxicity in the form of less induced TNFα and systemic disease.

The present invention provides compositions and methods for the genetic disruption of the msbB gene in bacteria, such as Salmonella, which results in bacteria, such as Salmonella, possessing a lesser ability to elicit TNFα and reduced virulence compared to the wild type. In one embodiment, the invention provides for improved methods for selecting genetic disruptions of the msbB gene. Additionally, the genetically modified bacteria have increased sensitivity to a chelating agent compared to bacteria with the wild type msbB gene. In a preferred embodiment, Salmonella having a disrupted msbB gene, which are hyperinvasive to tumor tissues, are able to replicate within the tumors, and are useful for inhibiting the growth and/or reducing the tumor volume of sarcomas, carcinomas, lymphomas or other solid tumor cancers, such as germ line tumors and tumors of the central nervous system, including, but not limited to, breast cancer, prostate cancer, cervical cancer, uterine cancer, lung cancer, ovarian cancer, testicular cancer, thyroid cancer, astrocytoma, glioma, pancreatic cancer, stomach cancer, liver cancer, colon cancer, and melanoma.

In an embodiment of the present invention, the bacteria are attenuated by other means, including but not limited biosynthetic pathway mutations leading to auxotrophy. In one specific embodiment, the biosynthetic pathway mutation is a genetic disruption of the purI gene. In another embodiment, the bacteria express pro-drug converting enzymes including but not limited to HSV-TK, cytosine deaminase (CD), and p450 oxidoreductase.

The present invention also provides a means for enhanced sensitivity for use in terminating therapy and for post therapy elimination. According to one embodiment of the present invention, the tumor-targeted bacteria having a genetically modified lipid A also have enhanced susceptibility to certain agents, e.g., chelating agents. It is a further advantage to modify tumor-targeted bacteria in this way because it increases the ability to eliminate the bacteria with agents which have an antibiotic-like effect, such as chelating agents including, but not limited to, Ethylenediaminetetraacetic Acid (EDTA), Ethylene Glycol-bis(β-aminoethyl Ether) N, N, N', N',-Tetraacetic Acid (EGTA), and sodium citrate. Modification to enhance the ability to eliminate the bacteria via exogenous means, such as the administration of an agent to which the genetically modified bacteria are more sensitive than their wild type counterparts, is therefore useful.

The present invention further provides for a Salmonella strain comprising deletion mutations in both the msbB gene as well as an auxotrophic gene. In a specific embodiment, the auxotrophic deletion mutation affects the purI gene. In a preferred embodiment, these mutations lead to increased safety of the strain. In another preferred embodiment, the strain also carries other mutations described herein which increase efficacy of the strain but are not essential for its safety.

4. DEFINITIONS

As used herein, Salmonella encompasses all Salmonella species, including: *Salmonella typhi, Salmonella choleraesuis,* and *Salmonella enteritidis.* Serotypes of Salmonella are also encompassed herein, for example, *typhimurium,* a subgroup of *Salmonella enteritidis,* commonly referred to as *Salmonella typhimurium.*

Attenuation: Attenuation is a modification so that a microorganism or vector is less pathogenic. The end result of attenuation is that the risk of toxicity as well as other side-effects is decreased, when the microorganism or vector is administered to the patient.

Virulence: Virulence is a relative term describing the general ability to cause disease, including the ability to kill normal cells or the ability to elicit septic shock (see specific definition below).

Septic shock: Septic shock is a state of internal organ failure due to a complex cytokine cascade, initiated by TNFα. The relative ability of a microorganism or vector to elicit TNFα is used as one measure to indicate its relative ability to induce septic shock.

Chelating agent sensitivity: Chelating agent sensitivity is defined as the effective concentration at which bacteria proliferation is affected, or the concentration at which the viability of bacteria, as determined by recoverable colony forming units (c.f.u.), is reduced.

5. BRIEF DESCRIPTION OF THE FIGURES

The present invention may be understood more fully by reference to the following detailed description, illustrative examples of specific embodiments and the appended figures.

FIG. 1. The complete DNA sequence of the Salmonella wild type (WT) 14028 msbB gene (SEQ ID NO:1) and the deduced amino acid sequence of the encoded protein (SEQ ID NO:2).

FIGS. 2A–2C. Knockout construct generated using the cloned Salmonella WT 14028 msbB gene. The cloned gene was cut with SphI and MluI thereby removing approximately half of the msbB coding sequence, and the tetracycline resistance gene (TET) from pBR322 cut with AatII and AvaI was inserted after blunt-ending using the Klenow fragment of DNA polymerase I. A =Knockout construct. B=Salmonella chromosomal copy of msbB. C=Salmonella disrupted chromosomal copy of msbB after homologous recombination. The start codon (ATG) and stop codon (TAA) and restriction sites AseI, BamHI, SphI, MluI, and EcoRV are shown. The position of two primers, P1 and P2 which generate two different sized PCR products for either wild type or disrupted msbB are shown.

FIGS. 3A–3C. Southern blot analysis of chromosomally disrupted Salmonella WT 14028 msbB. A) Southern blot probed with the tetracycline gene, demonstrating its presence in the plasmid construct and the two clones, and its absence in the WT 14028 bacteria. B) Southern blot of a similar gel probed with an $^{32}$P-labeled AseI/BamH1 fragment derived from the cloned msbB. The AseI enzyme cuts upstream of msbB, and the BamH1 cuts in one location in the wild type, but in a second location in the tetracycline gene which results in a higher molecular weight product. Lane 1 (KO) shows the position of the band in the knockout construct, compared to the WT 14028 in lane 2 (WT). Lanes 3 and 4 show the clones YS8211 and YS861 with a higher molecular weight product. C) Southern blot of a similar gel probed with an $^{32}$P-labeled MluI fragment derived from the cloned msbB. See text Section 7.2 for details.

Figure 4:
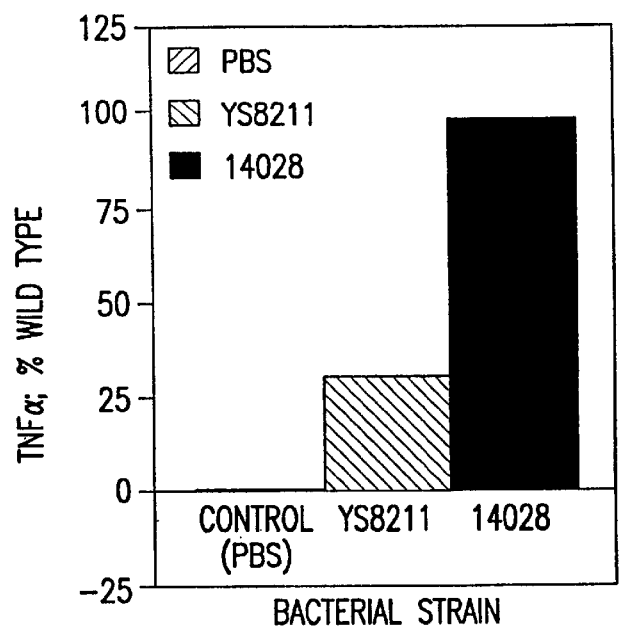

FIG. 4. TNFα induction by live Salmonella WT 14028 in mice. $1\times10^8$ live bacteria in 0.1 cc phosphate buffered saline of the wild type or msbB$^-$ disrupted strains were injected i.v. in the tail vein of Balb/c mice. The bar graph indicates the TNFα induction with error bars. Clone YS8211 induces TNFα 32% compared to Salmonella WT 14028.

Figure 5:
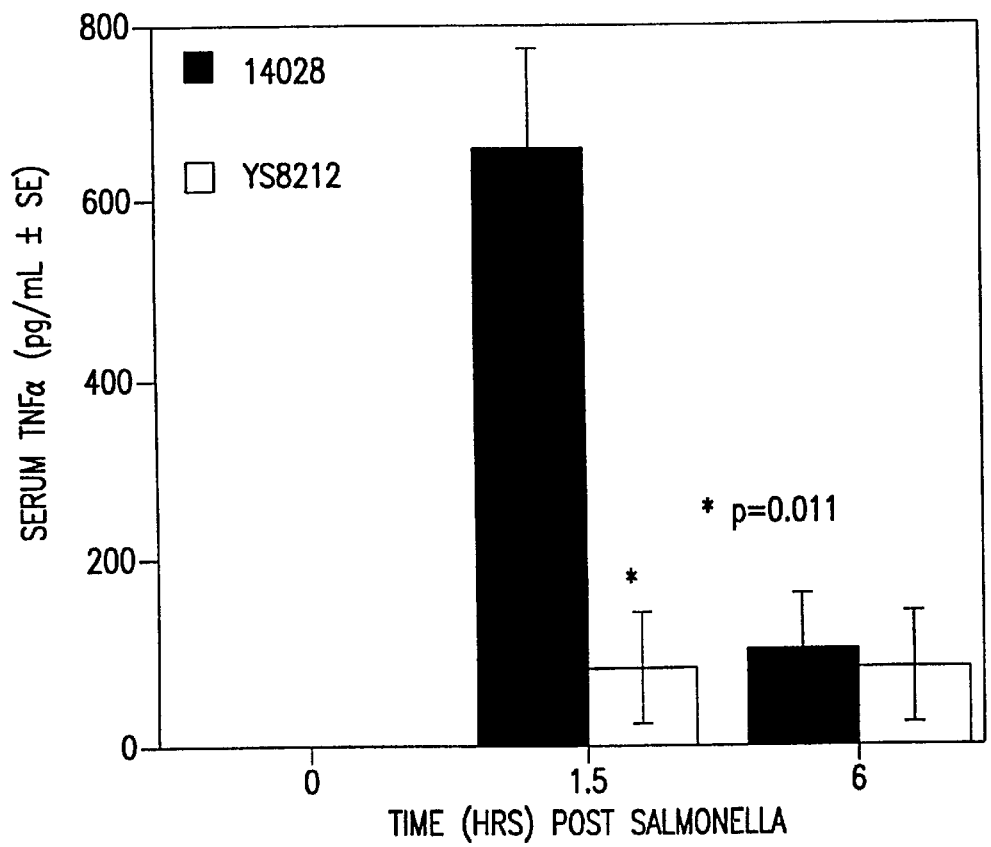

FIG. 5. TNFα response by Sinclair swine to live Salmonella WT 14028 and msbB$^-$ clone YS8212. TNFα levels were measured at 1.5 and 6.0 hours following i.v. introduction of 1×109 c.f.u. Salmonella WT 14028 and YS8212. At 1.5 hours TNFα response was significantly lower (p≦0.011) in the msbB deletion mutant compared to the wild type.

Figure 6A:
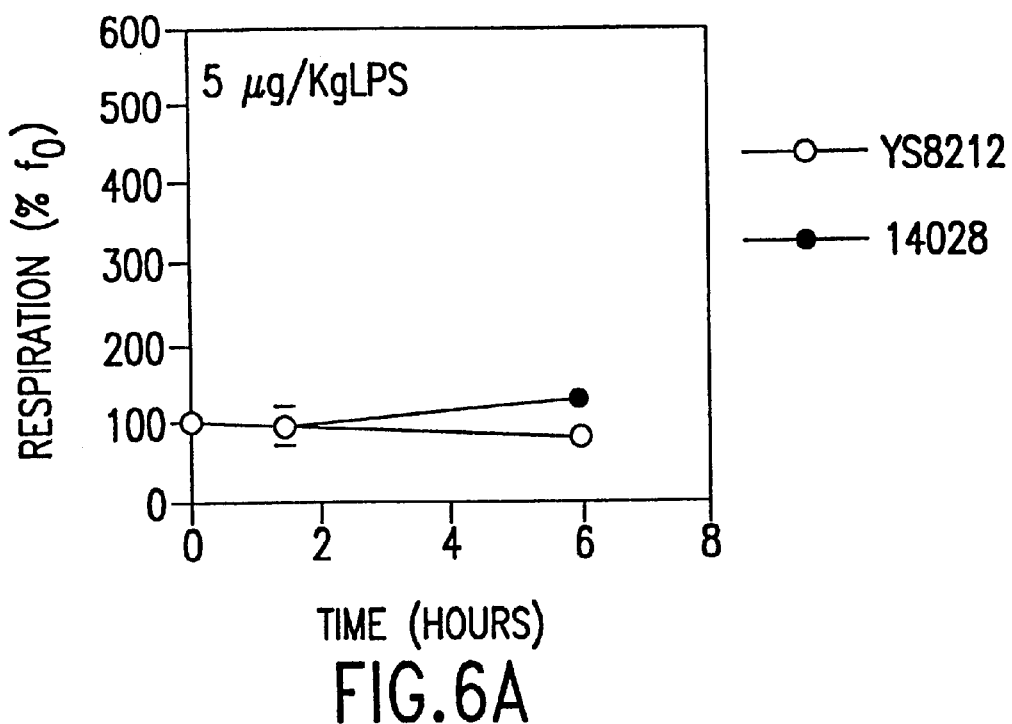
Figure 6B:
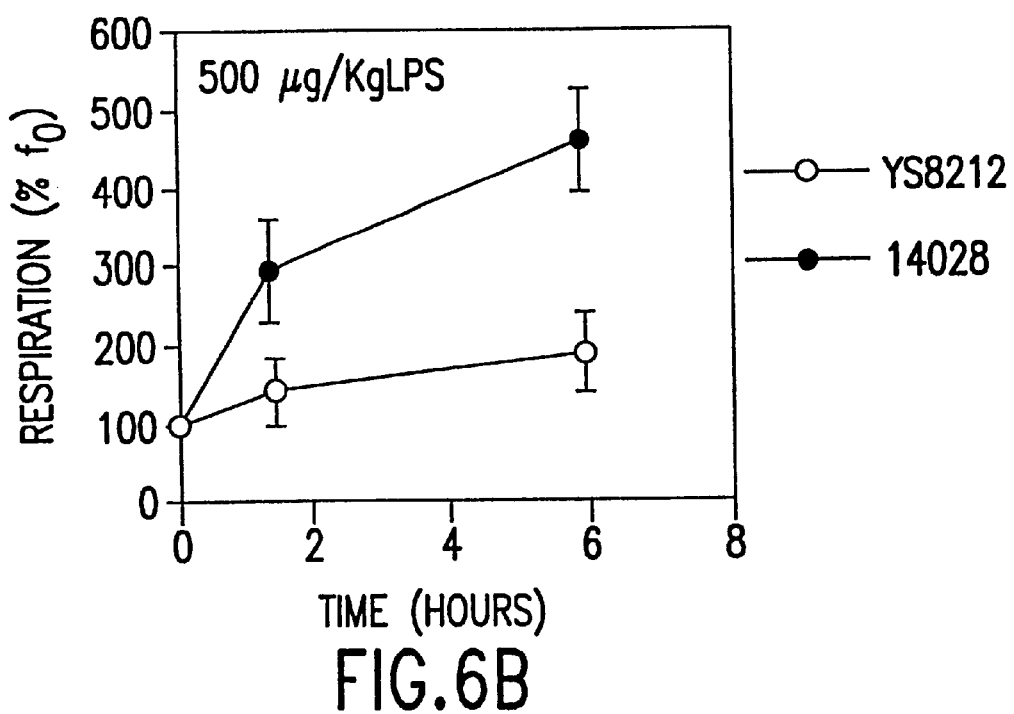

FIGS. 6A–6B. Respiratory level changes induced by LPS from WT 14028 and msbB⁻ clone YS8212. Sinclair swine were injected with A) 5 μg/kg purified LPS or B) 500 μg/kg purified LPS and respiration rate was determined. The 500 μg/kg of LPS from Salmonella WT 14028 raised the rate of respiration to more than 4 times normal, whereas the rate of respiration in msbB⁻ LPS-treated animals was less than doubled.

Figure 7:
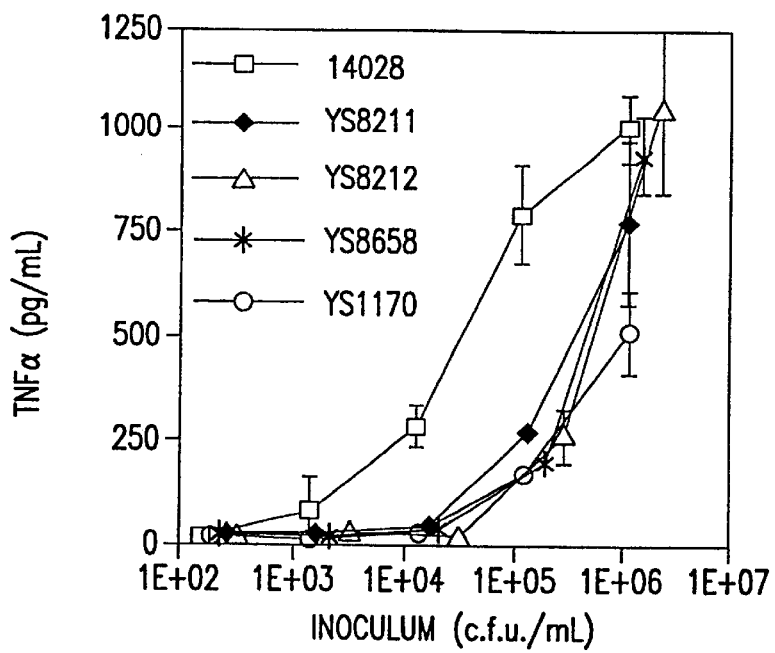

FIG. 7. TNFα induction by live Salmonella WT 14028 in human monocytes. Human monocytes isolated from peripheral blood were exposed to increasing amounts of Salmonella c.f.u. At $1.0 \times 10^5$ c.f.u., concentrations of TNFα induced by WT 14028 were more than 3 times higher than those induced by a number of msbB⁻ clones, i.e., YS8211, YS8212, YS8658, and YS1170.

Figure 8:
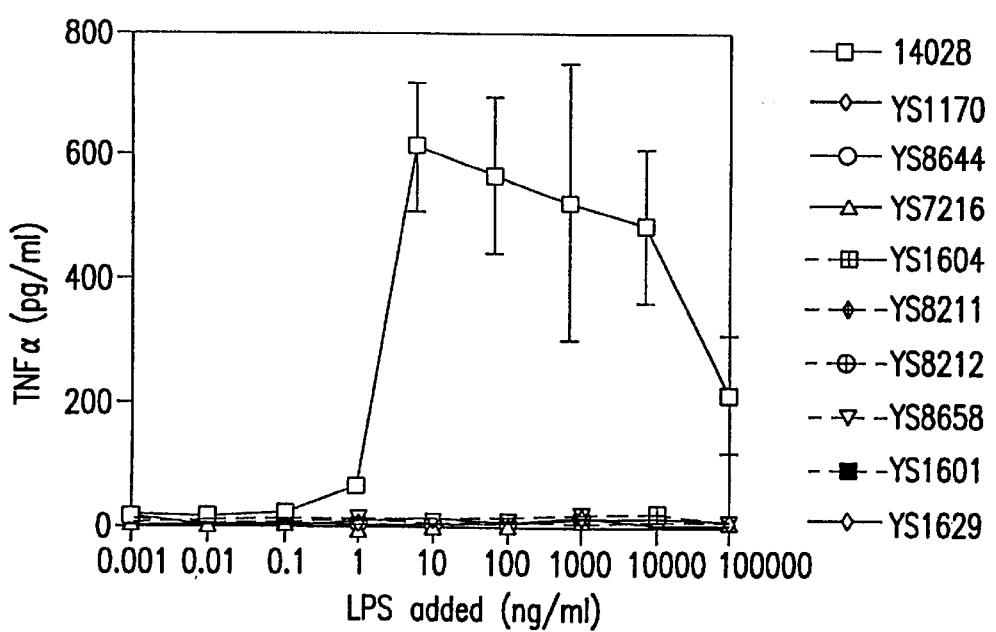

FIG. 8. TNFα production by human monocytes. Human monocytes isolated from peripheral blood were exposed to increasing amounts of purified LPS. As little as 1 nanogram of LPS from wild type was sufficient to elicit a measurable TNFα response and was maximal at 10 ng. In contrast, 100 μg of LPS from each of a number of msbB⁻ clones was insufficient to generate any response. Thus, at 10 ng LPS, the concentration of TNFα induced by Salmonella WT 14028 was at least $10^5$ times higher than concentrations of TNFα induced by the independent msbB knockouts, i.e., YS7216 and YS8211, and the derivatives, i.e., YS1170, YS8644, YS1604, YS8212, YS8658, YS1601, YS1629.

Figure 9A:
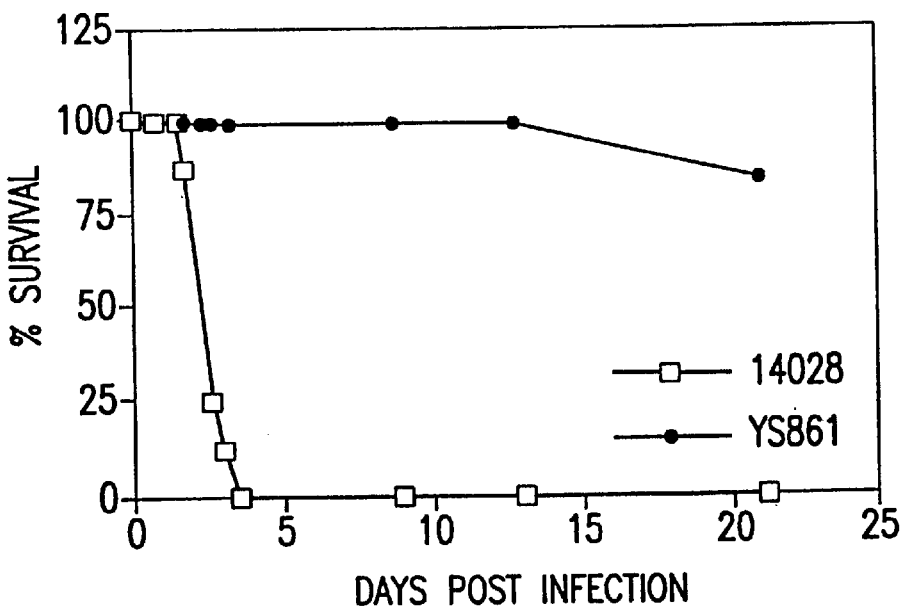
Figure 9B:
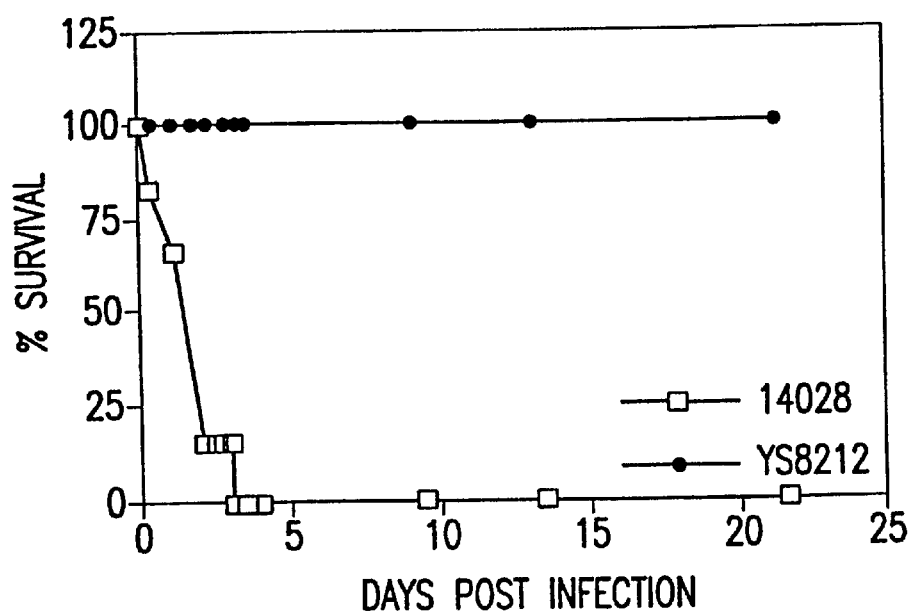

FIGS. 9A–9B. Survival of mice and Sinclair swine, injected with $2 \times 10^7$ or $1 \times 10^9$ respectively of live bacteria. A) WT 14028 killed all the mice in 4 days, whereas the msbB⁻ clone YS862 spared 90% of the mice past 20 days. B) Similarly, WT 14028 killed all the swine in 3 days, whereas the msbB⁻ clone YS8212 spared 100% of the swine past 20 days.

Figure 10:
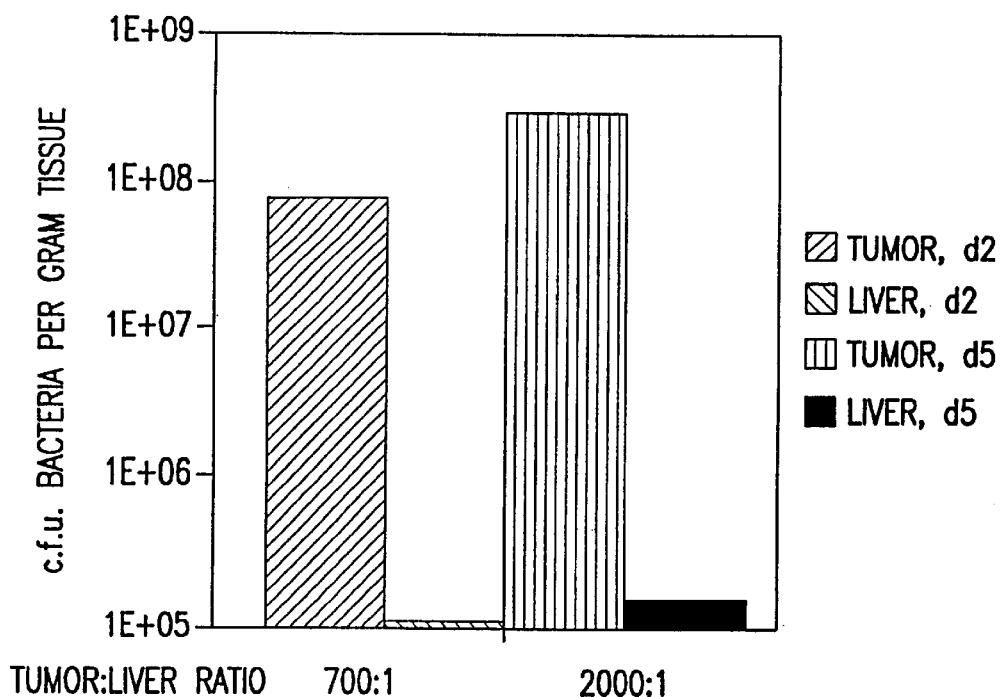

FIG. 10. Biodistribution of msbB⁻ Salmonella YS8211 in B16F10 melanoma tumors. At 5 days, the ratio of msbB⁻ Salmonella within the tumors compared to those in the liver exceeded 1000:1.

Figure 11:
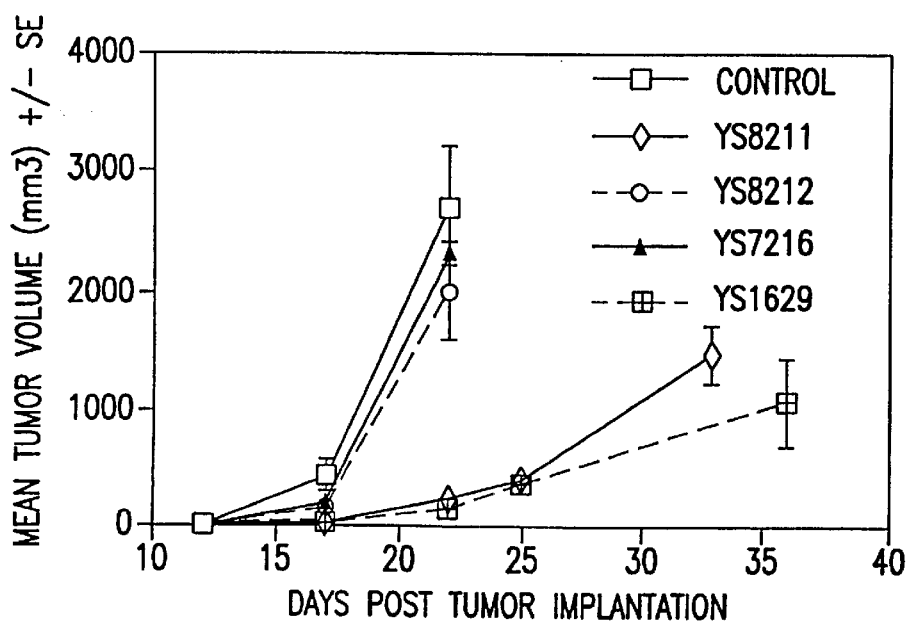

FIG. 11. Tumor retardation by msbB⁻ Salmonella. B16F10 melanoma tumors were implanted in the flank of C57BL/6 mice and allowed to progress to day 8. Mice either received no bacteria (control) or msbB⁻ strains YS8211, YS8212, YS7216, YS1629. Two of the strains, YS8211 and YS1629 retarded tumor progression significantly, whereas strains YS7216 and YS8212 did not.

Figure 12A:
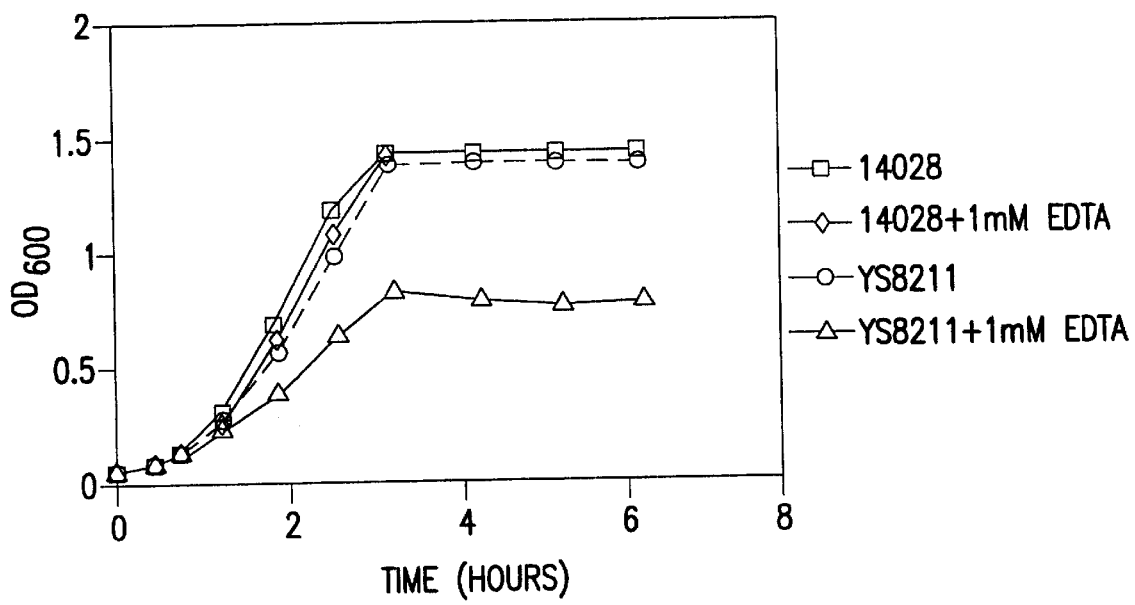
Figure 12B:
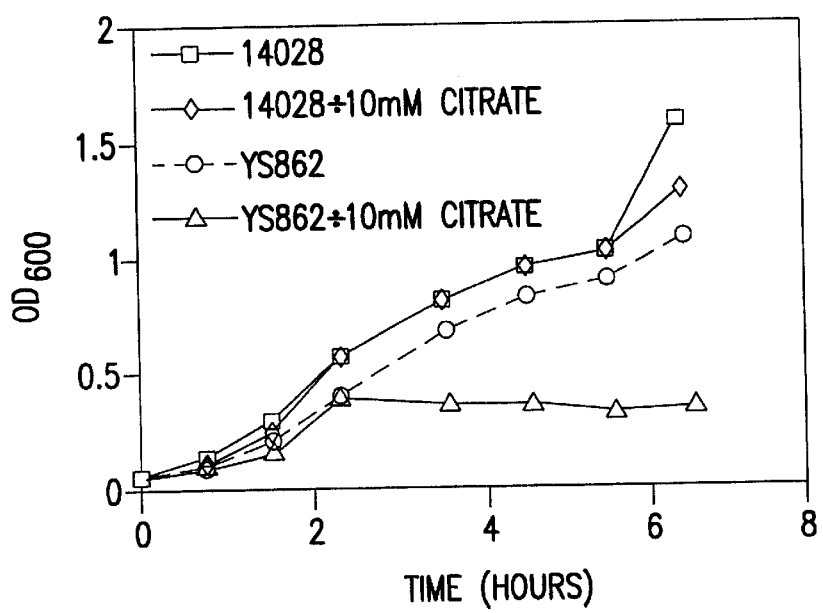

FIGS. 12A–12B. Sensitivity of WT 14028 and msbB disrupted bacteria to chelating agents. Wild type and msbB disrupted Salmonella clone YS8211 and YS862 were grown in LB broth lacking sodium chloride (LB-zero), in the presence or absence of 1 mM EDTA (FIG. 12A) or in the presence or absence of 10 mM sodium citrate (FIG. 12B). The $OD_{600}$ was determined and plotted as a function of time. The msbB+ strain showed little inhibition by EDTA or sodium citrate, compared to the msbB⁻ strains which showed near complete cessation of growth after 3 hours for EDTA or sodium citrate.

Figure 13A:
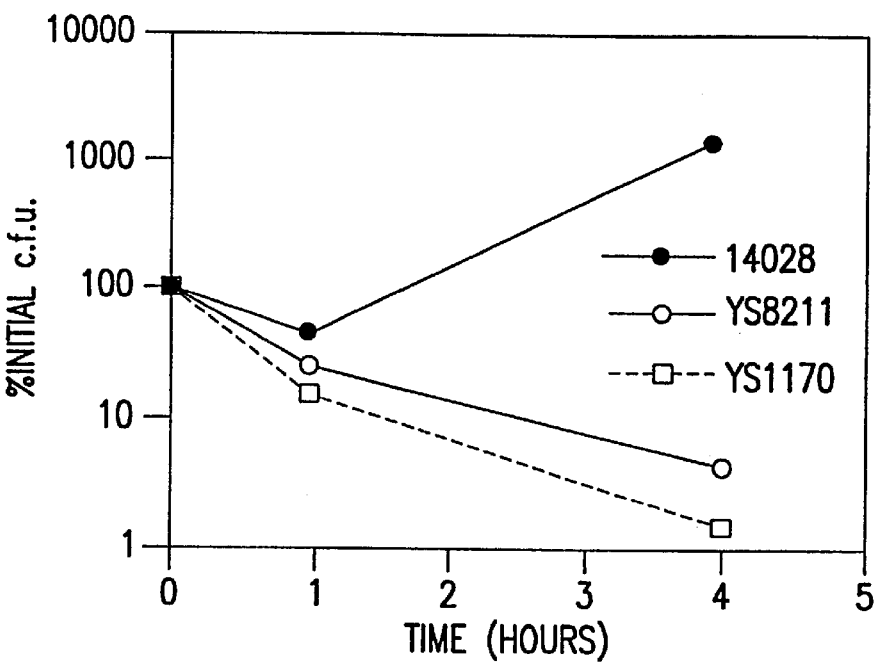
Figure 13B:
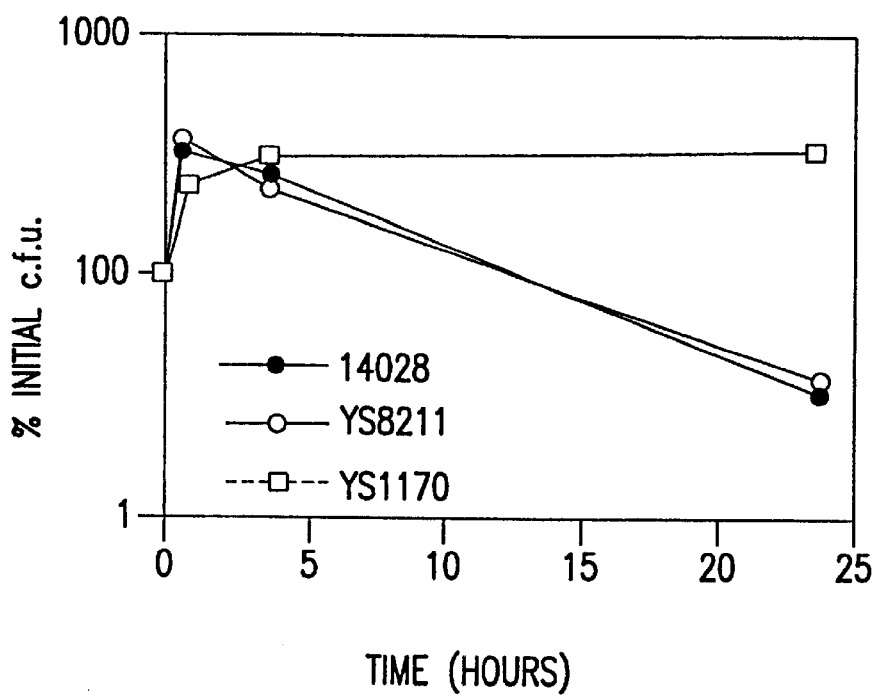

FIGS. 13A–13B. Survival of msbB⁻ bacteria within murine macrophages. Murine bone marrow-derived macrophages (FIG. 13A) and a murine macrophage cell line, J774, (FIG. 13B) were used as hosts for bacterial internalization and quantified over time. The data are presented as a percentage of initial c.f.u.

Figure 14:
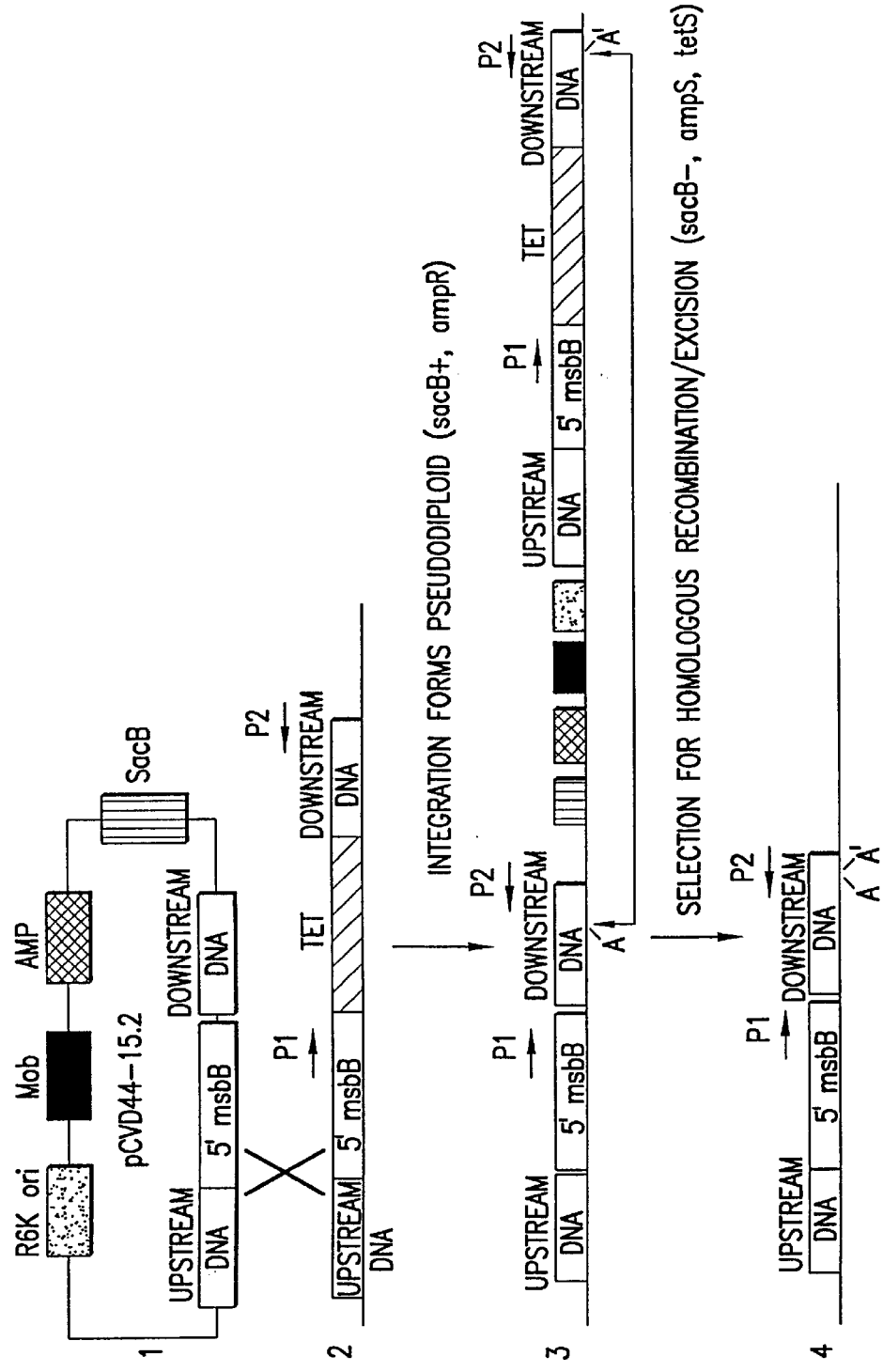

FIG. 14. Conversion of msbB1(Δ): :tet to tet$^s$ using the positive selection suicide vector pCVD442 carrying a second version of the msbB⁻ (msbB2(Δ) amp$^R$ sacB⁺).

Figure 15:
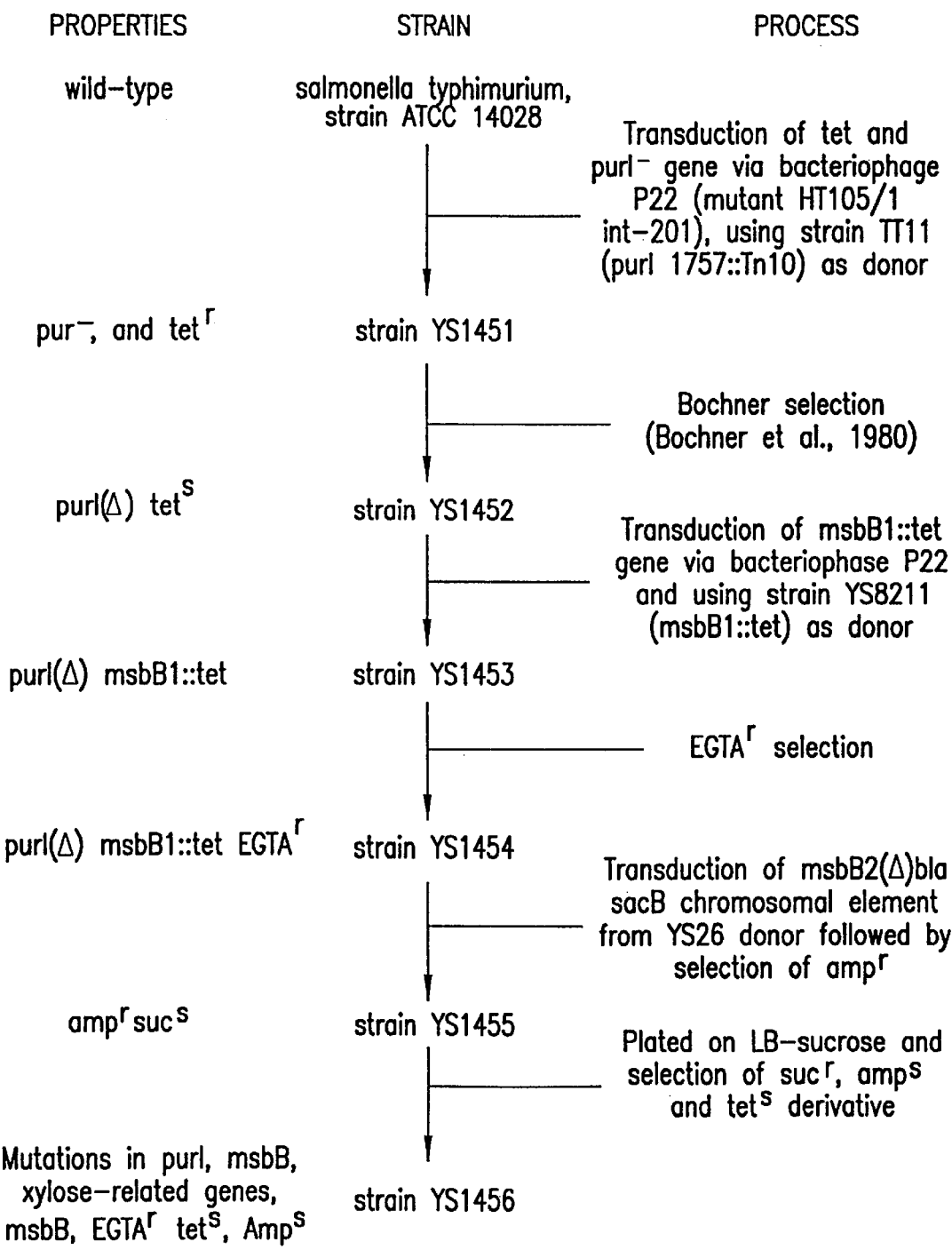

FIG. 15. Schematic diagram of the derivation of strain YS1456 from wild type *Salmonella typhimurium*. See text Section 8.1 for details.

Figure 16:
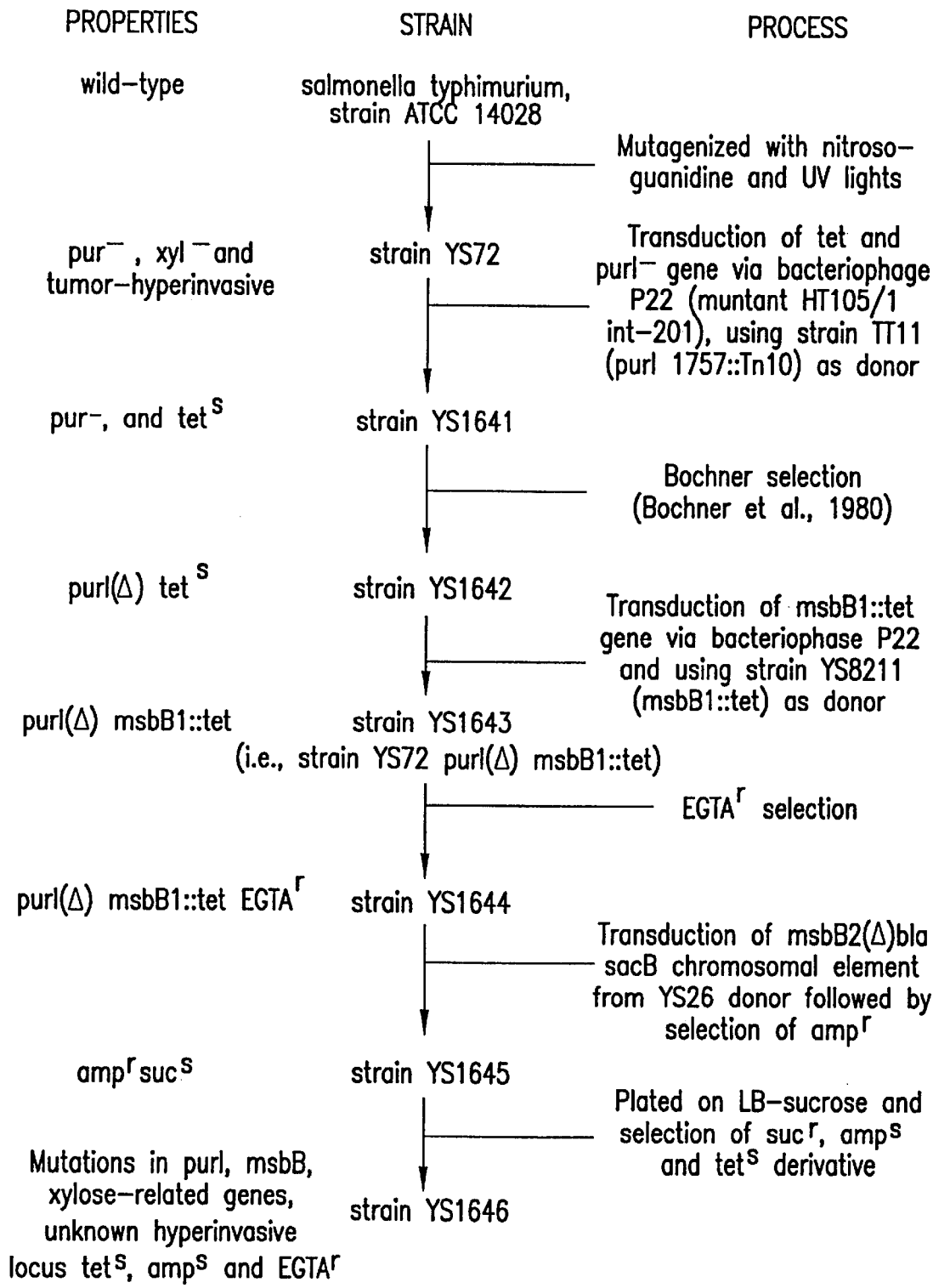

FIG. 16. Schematic diagram of the derivation of strain YS1646 from wild type *Salmonella typhimurium*. See text Section 8.2 for details.

Figure 17:
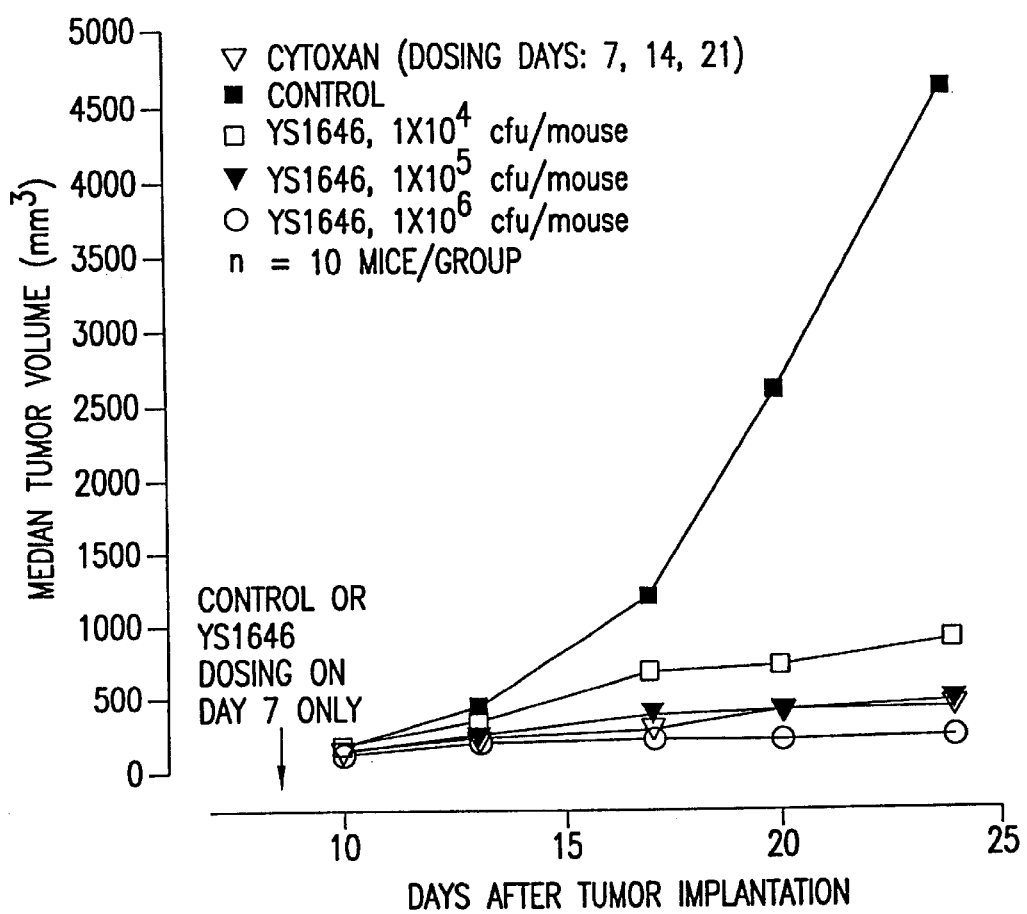

FIG. 17. Effect of YS1646 dose on B16-B10 murine melanoma tumor growth.

Figure 18:
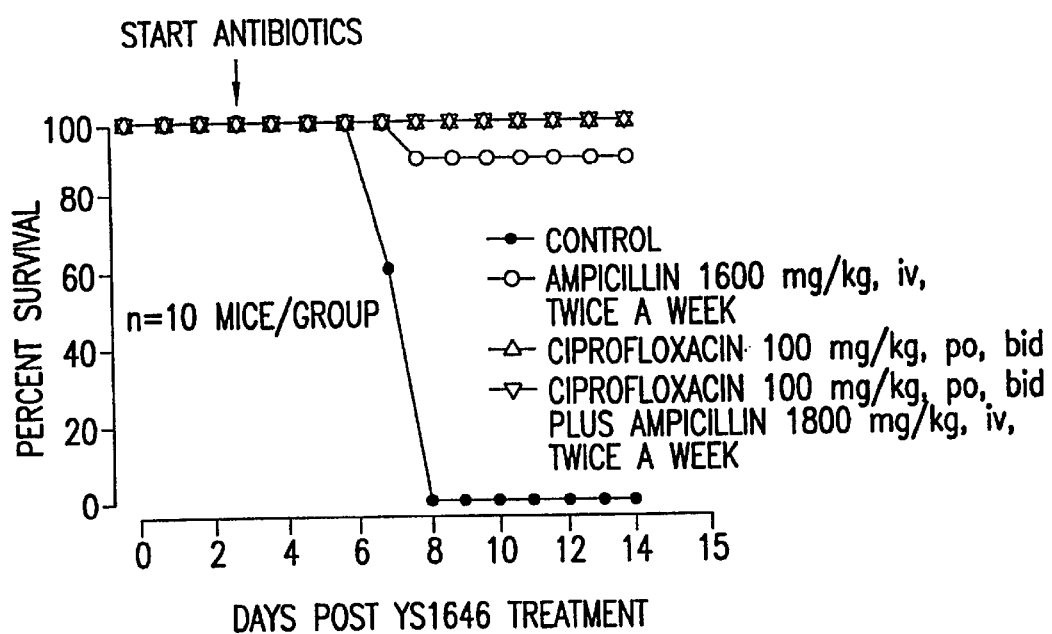

FIG. 18. Antibiotic suppression of YS1646-induced mortality following lethal infection.

6. DETAILED DESCRIPTION OF THE INVENTION

The present invention is based on the isolation of a gene of Salmonella, i.e., msbB, which, when present in its normal form, contributes to TNFα induction, general virulence, survival within macrophages, and insensitivity to certain agents which promote eradication of the bacteria. The present invention is directed to the genetic modification of the gene which results in disrupting the normal function of the product of the gene, and the incorporation of the genetic modification into tumor-targeted bacteria, including Salmonella, for therapeutic use. In a preferred embodiment, the bacteria have a genetic modification of the msbB gene as well as genetic modification of a gene in a biosynthetic pathway, such as the purI gene, resulting in an auxotrphic strain.

In a preferred embodiment, the genetically modified bacteria are used in animals, including humans, for reduction of volume and/or growth inhibition of solid tumors.

In an additional preferred embodiment, bacteria useful for the present invention show preference for attachment to and penetration into certain solid tumor cancer cells or have an enhanced propensity to proliferate in tumor tissues as compared to normal tissues. These bacteria, include but are not limited to Salmonella, having a natural ability to distinguish between cancerous or neoplastic cells tissues and normal cells/tissues.

Alternatively, tumor cell-specific bacteria useful for the invention may be selected for and/or improved in tumor targeting ability using the methods described by Pawelek et al., WO 96/40238 incorporated herein by reference. Pawelek et al. describe methods for isolating tumor cell-specific bacteria by cycling a microorganism through pre-selected target cells, preferably solid tumor cells in vitro, or through a solid tumor in vivo, using one or more cycles of infection.

6.1 ISOLATION/IDENTIFICATION OF A GENE INVOLVED IN VIRULENCE

The *E. coli* gene, msbB, has been shown to be involved in myristilization of lipid A (Somerville et al., 1996, J. Clin. Invest. 97:359–365.) The chromosomal organization of the *E. coli* msbB gene and the DNA sequence coding for the msbB gene have been described (Engel, et al., 1992, J. Bacteriol. 174:6394–6403; Karow and Georgopoulos, 1992, J. Bacteriol. 174: 702–710; Somerville et al., 1996, J. Clin. Invest. 97: 359–365).

As shown in the present invention, the msbB gene can be isolated from bacterial strains, other than *E. coli*, using low stringency DNA/DNA hybridization techniques known to those skilled in the art. (Sambrook et al., Molecular Cloning, Cold Spring Harbor Laboratory Press, 1989). For an illustrative example of isolation of a msbB gene of bacteria, including but not limited to Salmonella spp., see Section 7.1 infra. A bacterial DNA library can be probed with a $^{32}$p-labeled msbB gene from E. coli. Hybridizing clones are determined to be correct if they contain DNA sequences similar to the known E. coli msbB gene.

6.1.1 GENETIC ALTERATION OF SALMONELLA msbB

One embodiment of the present invention provides a composition of matter which is a strain of bacteria with a genetic alteration in the msbB gene. In a preferred embodiment, the bacteria is Salmonella sp. Genetic alteration in the form of disruption or deletion can be accomplished by several means known to those skilled in the art, including homologous recombination using an antibiotic resistance marker. These methods involve disruption of the plasmid-based, cloned msbB gene using restriction endonucleases such that part or all of the gene is disrupted or eliminated or such that the normal transcription and translation are interrupted, and an antibiotic resistance marker for phenotypic selection is inserted in the region of that deletion, disruption or other alteration. Linearized DNA is transformed into Salmonella, and bacteria bearing the antibiotic resistance are further examined for evidence of genetic alteration. Means for examining genetic alteration include PCR analysis and Southern blotting. For an illustrative example of genetic disruption of a Salmonella msbB gene, see Section 7.2.

In another embodiment of the invention, the msbB$^-$/antibiotic resistance marker can be transduced into a new bacterial strain. An illustrative example is provided in Section 7.2. Bacteriophage P22 and a Salmonella msbB$^-$ clone can be grown in zero salt Luria broth and the new phages in the supernate can be used to infect a new Salmonella strain.

Yet another embodiment of the present invention provides Salmonella that are attenuated in more than one manner, e.g., a mutation in the pathway for lipid A production, such as the msbB mutation described herein and one or more mutations to auxotrophy for one or more nutrients or metabolites, such as uracil biosynthesis, purine biosynthesis, and arginine biosynthesis as described by Bochner, 1980, J. Bacteriol. 143:926–933 herein incorporated by reference. In a preferred embodiment, the ability of msbB$^-$ Salmonella to accumulate within tumors is retained by msbB$^-$ Salmonella having one or more mutations resulting in an auxotrophic strain. In a more preferred mode of this embodiment of the invention, the bacterial vector which selectively targets tumors and expresses a pro-drug converting enzyme is auxotrophic for uracil, aromatic amino acids, isoleucine and valine and synthesizes an altered lipid A. In a specific preferred embodiment the msbB$^-$ Salmonella also contain a genetic modification of the biosynthetic pathway gene, purI, leading to decreased virulence of the strain compared to wild type. An illustrative example is provided in Sections 7 and 8.

6.1.2 CHARACTERISTICS OF SALMONELLA HAVING DISRUPTED msbB

A characteristic of the msbB$^-$ Salmonella, described herein, is decreased ability to induce a TNFα response compared to the wild type bacterial vector. Both the whole bacteria and isolated or purified lipopolysaccharide (LPS) elicit a TNFα response. In an embodiment of the invention, the msbB$^-$ Salmonella induce TNFα expression at about 5 percent to about 40 percent compared to the wild type Salmonella sp. (in other words, the msbB$^-$ Salmonella induce TNFα expression at about 5 percent to about 40 percent of the level induced by wild type Salmonella, e.g., WT 14028.) In a preferred embodiment of the invention, the msbB$^-$ Salmonella induce TNFα expression at about 10 percent to about 35 percent of that induced by a wild type Salmonella sp. In an embodiment of the invention, purified LPS from msbB$^-$ Salmonella induces TNFα expression at a level which is less than or equal to 0.001 percent of the level induced by LPS purified from wild type Salmonella sp. TNFα response induced by whole bacteria or isolated or purified LPS can be assessed in vitro or in vivo using commercially available assay systems such as by enzyme linked immunoassay (ELISA). For illustrative examples, see sections 7.3.1 and 7.3.2 infra. Comparison of TNFα production on a per c.f.u. or on a μg/kg basis, is used to determine relative activity. Lower TNFα levels on a per unit basis indicate decreased induction of TNFα production.

REDUCTION OF VIRULENCE

Another characteristic of the msbB$^-$ Salmonella, described herein, is decreased virulence towards the host cancer patient compared to the wild type bacterial vector. Wild type Salmonella can under some circumstances exhibit the ability to cause significant progressive disease. Acute lethality can be determined for normal wild type live Salmonella and live msbB$^-$ Salmonella using animal models. For an illustrative example, see Section 7.4 and Section 9, Table III. Comparison of animal survival for a fixed inoculum is used to determine relative virulence. Strains having a higher rate of survival have decreased virulence.

DECREASED SURVIVAL WITHIN MACROPHAGES

Another characteristic of msbB$^-$ Salmonella described herein, is decreased survival within macrophage cells as compared to survival of wild type bacteria. Wild type Salmonella (e.g., ATCC 14028) are noted for their ability to survive within macrophages (Baumler, et al., 1994, Infect. Immun. 62:1623–1630; Buchmeier and Heffron 1989, Infect. Immun. 57:1–7; Buchmeier and Heffron, 1990, Science 248:730–732; Buchmeier et al., 1993, Mol. Microbiol. 7:933–936; Fields et al., 1986, Proc. Natl. Acad. Sci. USA 83:5189–93; Fields et al., 1989, Science 243:1059–62; Fierer et al., 1993, Infect. Immun. 61:5231–5236; Lindgren et al., 1996, Proc. Natal. Acad. Sci. USA 3197–4201; Miller et al., 1989, Proc. Natl. Acad. Sci. USA 86:5054–5058; Sizemore et al., 1997, Infect. Immun. 65:309–312).

A comparison of survival time in macrophages can be made using an in vitro cell culture assay. A lower number of c.f.u. over time is indicative of reduced survival within macrophages. For an illustrative example, see Section 8 infra. As shown therein, using the gentamicin-based internalization assay and bone marrow-derived murine macrophages or the murine macrophage cell line J774, a comparison of survival of WT 14028 and msbB$^-$ clone YS8211 was determined. In an embodiment of the invention, survival occurs at about 50 percent to about 30 percent; preferably at about 30 percent to about 10 percent; more preferably at about 10 percent to about 1 percent of survival of the wild type stain.

INCREASED SENSITIVITY

Another characteristic of one embodiment of the msbB$^-$ Salmonella, described herein, is increased sensitivity of the tumor-targeted bacteria to specific chemical agents which is advantageously useful to assist in the elimination of the bacteria after administration in vivo. Bacteria are susceptible to a wide range of antibiotic classes. However, it has surprisingly been discovered that certain Salmonella msbB⁻ mutants encompassed by the present invention are sensitive to certain chemicals which are not normally considered antibacterial agents. In particular, certain msbB⁻ Salmonella mutants are more sensitive than WT 14028 to chelating agents.

Previous descriptions of msbB⁻ *E. coli* have not suggested increased sensitivity to such chelating agents. To the contrary, reports have included increased resistance to detergents such as deoxycholate (Karow and Georgopoulos 1992 J. Bacteriol. 174: 702–710).

To determine sensitivity to chemical agents, normal wild type bacteria and msbB⁻ bacteria are compared for growth in the presence or absence of a chelating agent, for example, EDTA, EGTA or sodium citrate. Comparison of growth is measured as a function of optical density, i.e., a lower optical density in the msbB- strain grown in the presence of an agent, than when the strain is grown in its absence, indicates sensitivity. Furthermore, a lower optical density in the msbB⁻ strain grown in the presence of an agent, compared to the msbB⁺ strain grown in its presence, indicates sensitivity specifically due to the msbB mutation. For an illustrative example, see section 7.7 infra. In an embodiment of the invention, 90 percent inhibition of growth of msbB⁻ Salmonella (compared to growth of wild type Salmonella sp.) occurs at about 0.25 mM EDTA to about 0.5 mM EDTA, preferably at about 99 percent inhibition at about 0.25 mM EDTA to above 0.5 mM EDTA, more preferably at greater than 99 percent inhibition at about 0.25 mM EDTA to about 0.5 mM EDTA. Similar range of growth inhibition is observed at similar concentrations of EGTA.

DERIVATIVES OF msbB MUTANTS

When grown in Luria Broth (LB) containing zero salt, the msbB⁻ mutants of the present invention are stable, i.e., produce few derivatives (as defined below). Continued growth of the msbB⁻ mutants on modified LB (10 g tryptone, 5 g yeast extract, 2 ml 1N CaCl₂, and 2 ml 1N MgSO₄ per liter, adjusted to pH 7 using 1N NaOH) also maintains stable mutants.

In contrast, when grown in normal LB, the msbB⁻ mutants may give rise to derivatives. As used herein, "derivatives" is intended to mean spontaneous variants of the msbB⁻ mutants characterized by a different level of virulence, tumor inhibitory activity and/or sensitivity to a chelating agent when compared to the original msbB⁻ mutant. The level of virulence, tumor inhibitory activity, and sensitivity to a chelating agent of a derivative may be greater, equivalent, or less compared to the original msbB⁻ mutant.

Derivatives of msbB⁻ strains grow faster on unmodified LB than the original msbB⁻ strains. In addition, derivatives can be recognized by their ability to grow on MacConkey agar (an agar which contains bile salts) and by their resistance to chelating agents, such as EGTA and EDTA. Derivatives can be stably preserved by cryopreservation at −70° C. or lyophilization according to methods well known in the art (Cryz et al., 1990, In New Generation Vaccines, M. M. Levine (ed.), Marcel Dekker, New York pp. 921–932; Adams, 1996, In Methods in Molecular Medicine: Vaccine Protocols, Robinson et al. (eds), Humana Press, New Jersey, pp. 167–185; Griffiths, Id. pp. 269–288.)

Virulence is determined by evaluation of the administered dose at which half of the animals die ($LD_{50}$). Comparison of the $LD_{50}$ of the derivatives can be used to assess the comparative virulence. Decrease in the $LD_5$ of a spontaneous derivative as compared to its msbB⁻ parent, indicates an increase in virulence. In an illustrative example, the faster-growing derivatives either exhibit the same level of virulence, a greater level of virulence, or a lower level of virulence compared to their respective original mutant strains (see Section 9, Table III.) In another example, the ability of a derivative to induce TNFα remains the same as the original mutant strain (see Section 7.3, FIG. 7).

In an illustrative example, the derivatives can either inhibit tumor growth more than or less than their respective original mutant strains (see Section 7.6, FIG. 11). It is demonstrated in Section 7.6 that the original msbB⁻ mutant, YS8211, significantly inhibits tumor growth whereas a derivative of this clone, YS8212, has less tumor growth inhibition activity. In contrast, the derivative, YS1629, exhibits enhanced tumor growth inhibition activity compared to its parent msbB⁻ clone, YS7216.

A derivative which is more virulent than its parent mutant but which does induce TNFα at a lower level when compared to the wild type, i.e., at a level of about 5 percent to about 40 percent of that induced by the wild type Salmonella, can be further modified to contain one or more mutations to auxotrophy. In an illustrative example, the YS1170 derivative is mutated such that it is auxotrophic for one or more aromatic amino acids, e.g., aroA, and thus can be made less virulent and is useful according to the methods of the present invention. In an additional illustrative example, genetic modifications of the purI gene (involved in purine biosynthesis) yeild Salmonella strains that are less virulent than the parent strain. (See Sections 7 and 8).

Prior to use of a derivative in the methods of the invention, the derivative is assessed to determine its level of virulence, ability to induce TNFα, ability to inhibit tumor growth, and sensitivity to a chelating agent.

6.2 USE OF SALMONELLA WITH DISRUPTED msbB FOR TUMOR TARGETING AND IN VIVO TREATMENT OF SOLID TUMORS According to the present invention, the msbB⁻ mutant Salmonella are advantageously used in methods to produce a tumor growth inhibitory response or a reduction of tumor volume in an animal including a human patient having a solid tumor cancer. For such applications, it is advantageous that the msbB⁻ mutant Salmonella possess tumor targeting ability or target preferably to tumor cells/tissues rather than normal cells/tissues. Additionally, it is advantageous that the msbB⁻ mutant Salmonella possess the ability to retard or reduce tumor growth and/or deliver a gene or gene product that retards or reduces tumor growth. Tumor targeting ability can be assessed by a variety of methods known to those skilled in the art, including but not limited to cancer animal models.

For example, Salmonella with a msbB⁻ modification are assayed to determine if they possess tumor targeting ability using the B16F10 melanoma subcutaneous animal model. A positive ratio of tumor to liver indicates that the genetically modified Salmonella possesses tumor targeting ability. For an illustrative example, see Section 7.5.

Salmonella with the msbB⁻ modification can be assayed to determine if they possess anti-tumor ability using any of a number of standard in vivo models, for example, the B16F10 melanoma subcutaneous animal model. By way of an illustrative example, and not by way of limitation, tumors are implanted in the flanks of mice and staged to day 8 and then bacterial strains are injected i.p.. Tumor volume is monitored over time. Anti-tumor activity is determined to be present if tumors are smaller in the bacteria-containing groups than in the untreated tumor-containing animals. For an illustrative example, see section 7.6 infra.

The Salmonella of the present invention for in vivo treatment are genetically modified such that, when administered to a host, the bacteria is less toxic to the host and easier to eradicate from the host's system. The Salmonella are super-infective, attenuated and specific for a target tumor cell. In a more preferred embodiment, the Salmonella may be sensitive to chelating agents having antibiotic-like activity.

In addition, the Salmonella used in the methods of the invention can encode "suicide genes", such as pro-drug converting enzymes or other genes, which are expressed and secreted by the Salmonella in or near the target tumor. Table 2 of Pawelek et al. WO96/40238 at pages 34–35 presents an illustrative list of pro-drug converting enzymes which are usefully secreted or expressed by msbB⁻ mutant Salmonella for use in the methods of the invention. Table 2 and pages 32–35 are incorporated herein by reference. The gene can be under the control of either constitutive, inducible or cell-type specific promoters. See Pawelek et al. at pages 35–43, incorporated herein by reference, for additional promoters, etc. useful for mutant Salmonella for the methods of the present invention. In a preferred embodiment, a suicide gene is expressed and secreted only when a Salmonella has invaded the cytoplasm of the target tumor cell, thereby limiting the effects due to expression of the suicide gene to the target site of the tumor.

In a preferred embodiment, the Salmonella, administered to the host, expresses the HSV TK gene. Upon concurrent expression of the TK gene and administration of ganciclovir to the host, the ganciclovir is phosphorylated in the periplasm of the microorganism which is freely permeable to nucleotide triphosphates. The phosphorylated ganciclovir, a toxic false DNA precursor, readily passes out of the periplasm of the microorganism and into the cytoplasm and nucleus of the host cell where it incorporates into host cell DNA, thereby causing the death of the host cell.

The method of the invention for inhibiting growth or reducing volume of a solid tumor comprises administering to a patient having a solid tumor, an effective amount of an isolated mutant Salmonella sp. comprising a genetically modified msbB gene, said mutant being capable of targeting to the solid tumor when administered in vivo. The msbB⁻ mutant Salmonella may also express a suicide gene as described above.

In addition, in one embodiment the isolated Salmonella is analyzed for sensitivity to chelating agents to insure for ease in eradication of the Salmonella from the patient's body after successful treatment or if the patient experiences complications due to the administration of the isolated Salmonella. Thus, if Salmonella is employed which is sensitive to a chelating agent, at about 0.25 mM to about 1.0 mM of a chelating agent such as EGTA, EDTA or sodium citrate can be administered to assist in eradication of the Salmonella after the anti-tumor effects have been achieved.

When administered to a patient, e.g., an animal for veterinary use or to a human for clinical use, the mutant Salmonella can be used alone or may be combined with any physiological carrier such as water, an aqueous solution, normal saline, or other physiologically acceptable excipient. In general, the dosage ranges from about 1.0 c.f.u./kg to about $1 \times 10^{10}$ c.f.u./kg; optionally from about 1.0 c.f.u./kg to about $1 \times 10^{8}$ c.f.u./kg; optionally from about $1 \times 10^{2}$ c.f.u./kg to about $1 \times 10^{8}$ c.f.u./kg; optionally from about $1 \times 10^{4}$ c.f.u./kg to about $1 \times 10^{8}$ c.f.u./kg.

The mutant Salmonella of the present invention can be administered by a number of routes, including but not limited to: orally, topically, injection including, but limited to intravenously, intraperitoneally, subcutaneously, intramuscularly, intratumorally, i.e., direct injection into the tumor, etc.

The following series of examples are presented by way of illustration and not by way of limitation on the scope of the invention.

7. EXAMPLE: LOSS OF VIRULENCE, REDUCED TNFα STIMULATION, AND INCREASED CHELATING AGENT SENSITIVITY, BY DISRUPTION OF THE SALMONELLA msbB

7.1 ISOLATION AND COMPOSITION OF SALMONELLA msbB GENE

A Salmonella genomic DNA library was first constructed. Wild type Salmonella typhimurium (ATCC strain 14028) were grown overnight and genomic DNA extracted according to the methods of Sambrook et al. (Molecular Cloning: A Laboratory Manual, 2nd Ed., Cold Spring Harbor Press, Cold Spring Harbor, 1989). Size-selected restriction endonuclease-digested fragments ranging from 2 to 10 kB were generated by time-limited digestion with Sau3A and selected by agarose gel electrophoresis. These fragments were ligated into pBluescript SK– and transformed to E. coli DH5α. Random analysis of clones revealed DNA inserts in ≧87%, with average size=5.1 Kb. The library consisted of $1.4 \times 10^{4}$ independent clones. In order to reduce the hybridization of the E. coli-originated msbB probe, to the 100% homologous chromosomal gene in E. coli, the entire library was harvested from the petri dishes by flooding them with phosphate buffered saline and using a glass rod to dislodge the colonies, and the resulting bacterial population was subjected to a large-scale plasmid isolation, resulting in an amplified Salmonella library plasmid pool. This plasmid pool was then transformed to Salmonella LT2 YS5010, thereby eliminating the E. coli background.

A probe for msbB homologues was generated using a clone of the E. coli msbB gene (Karow and Georgopoulos 1992 J. Bacteriol. 174: 702–710) by digesting E. coli with BglII/HincII and isolating a 600 bp fragment which corresponds to a portion of the coding sequence. This fragment was labeled using $\alpha^{32}$P-dCTP and used to probe the Salmonella library at low-stringency conditions consisting of 6× SSC, 0.1% SDS, 2× Denhardts, 0.5% non-fat dry milk overnight at 55° C. Strongly hybridizing colonies were purified, and plasmids extracted and subjected to restriction digestion and in situ gel hybridization under the same conditions used for colony hybridization (Ehtesham and Hasnain 1991 BioTechniques 11: 718–721). Further restriction digests revealed a 1.5 kB fragment of DNA which strongly hybridized with the probe and was sequenced at the Yale University Boyer Center using fluorescent dye termination thermal cycle sequencing. Sequence analysis revealed that the 1.5 kb fragment contained an msbB homologue which apparently lacked an initiating methionine corresponding to that of the E. coli gene. A probe consisting of the 5' region of this clone was generated by performing restriction digests using EcoR1/XbaI and again hybridizing to the library. The complete nucleotide sequence of the Salmonella msbB gene (SEQ ID NO:1) and the deduced amino acid sequence of the encoded protein (SEQ ID NO:2) is shown in FIG. 1. The DNA homology of the putative Salmonella msbB and the *E. coli* msbB is 75%. The protein homology is 98%, confirming that the cloned Salmonella gene is a bona fide msbB.

7.2 GENETIC ALTERATION OF SALMONELLA msbB

A knockout construct was generated using the cloned Salmonella msbB gene. The cloned gene was cut with SphI and MluI, thereby removing approximately half of the msbB coding sequence, and the tetracycline resistance gene from pBR322, out with AatII and AvaI, was inserted after blunt-ending using the Klenow fragment of DNA polymerase I (FIGS. 2A–2C). The knockout disruption was accomplished by homologous recombination procedures (Russell et al., 1989, J. Bacteriol. 171:2609); the construct was linearized using SacI and KpnI, gel purified and transfected to Salmonella LT2 YS501 by electroporation. Bacteria from the transformation protocol were first selected on tetracycline plates, and subsequently examined for the presence of plasmid-containing non-chromosomal integrated contaminants by ampicillin resistance and the presence of plasmids as determined by standard plasmid mini-preps (Titus, D. E., ed. *Promega Protocols and Applications Guide*, Promega Corp, 1991). Bacterial colonies which were tetracycline resistant yet lacked plasmids were subjected to a PCR-based analysis of the structure of their msbB gene. PCR was used with primers which generate a fragment inclusive of the region into which the tetracycline gene was inserted, where the forward primer was GTTGACTGGGAAGGTCTGGAG (SEQ ID NO:3), corresponding to bases 586 to 606, and the reverse primer was CTGACCGCGCTCTATCGCGG (SEQ ID NO:4), corresponding to bases 1465 to 1485. Wild type Salmonella msbB+ results in an approximately 900 base pair product, whereas the disrupted gene with the tetracycline insert results in an approximately 1850 base pair product. Several clones were obtained where only the larger PCR product was produced, indicating that the disruption in the msbB gene had occurred.

Southern blot analysis was used to confirm the disruption of the chromosomal copy of Salmonella msbB. The plasmid-based knockout construct (KO) was compared with genomic DNA prepared from wild type and putative disrupted msbB clones, YS82, YS86, YS8211 and YS861. The DNA was double digested with AseI/BamHI and separated by agarose gel electrophoresis on 0.9% or 1.2% agarose. Results of YS8211 and YS861 are presented in FIGS. 3A–3C. Similar gels were subjected to three separate criteria: 3A) the presence of the tetracycline gene when probed with an $^{32}$P-labeled tetracycline gene fragment, 3B) Restriction fragment length when probed with an $^{32}$P-labeled AseI/BamH1 fragment derived from the cloned msbB and 3C) the presence or absence of the msbB MluI fragment removed in order to disrupt the msbB gene and insert the tetracycline gene (FIGS. 3A–3C). Since the MluI fragment was removed in order to disrupt the msbB gene and insert the tetracycline gene, it is expected that this probe would hybridize with the wild type FIG. 3C (lane 2 WT) but not the knockout construct (lane 1 KO), or the clones, (lanes 3 and 4 YS8211 and YS821) thereby confirming the genetic alteration of the msbB gene. Each of the clones examined exhibited all of the expected criteria for an msbB gene deletion (knockout). These data further confirm that msbB exists as a single copy in the wild type Salmonella, as no other hybridizing bands were observed when probed with a labeled oligonucleotide derived from the cloned DNA.

After the msbB mutation was confirmed, additional strains containing the msbB$^-$ mutation were generated. The Salmonella strains used included WT 14028 and YS72 (pur$^-$ xyl$^-$ hyperinvasive mutant from WT 14028; Pawelek et al., WO 96/40238). P22 transduction was used to generate YS8211 (msbB::tet) using YS82 as a donor and YS861 and YS862 (msbB1::tet) using YS86 as a donor; all with WT 14028 as recipient. YS7216 (msbB1::tet from YS72) was generated by transduction using YS82 as a donor. Several derivatives are encompassed by the present invention, including but not limited to derivatives of YS8211 (YS8212, YS1170), YS862 (YS8644, YS8658), and YS7216 (YS1601, YS1604, YS1629). In a preferred embodiment, spontaneous derivatives grow somewhat faster on Luria agar compared to WT 14028 or msbB$^-$ clones generated by transduction. msbB$^+$ strains were grown in LB broth or on LB plates containing 1.5% agar at 37° C. msbB$^-$ strains were grown in modified LB containing 10 g tryptone, 5 g yeast extract, 2 ml 1N CaC$_2$ and 2 ml 1N MgSO$_4$ per liter, adjusted to pH 7 using 1N NaOH. For transducing msbB1::tet, LB lacking NaCl was used, with 4 mg/l tetracycline. Liquid cultures were shaken at 225 rpm. For tumor targeting experiments, cells were diluted 1:100 in LB, grown to OD$_{600}$=0.8 to 1.0, washed in phosphate buffered saline (PBS), and resuspended in PBS.

7.2.1 AN IMPROVED METHOD FOR SELECTING msbB GENETIC ALTERATIONS BY PRE-SELECTION WITH SUCROSE An improved method for selecting msbB genetic alterations by pre-selection with sucrose has been discovered. This pre-selection method is based on the selection of colonies that retain the sacB gene. The sacB gene is responsible for the conversion of sucrose into a toxic chemical, levan, that is lethal to the host cells, and can therefore be used to select for recombinants. Only those strains that undergo deletion of the sacB gene survive on medium containing sucrose and therefore have the sucrose resistance property suc$^r$. As described below, pre-selecting of colonies that retain the sacB gene, eliminated the need for dilutions and comparison of sucrose$^{(+)}$ vs. success$^{(-)}$ colonies as performed in the normal sucrose selection.

The normal selection procedure for the sucrase system

*E. coli* SM10 λpir carrying a plasmid with the msbB(Δ) bla and sacB genes was used as a donor. The bla gene for betalactamase confers resistance to ampicillin. In the normal selection procedure, the donor strain was mated using standard mating procedures, with a Salmonella strain into which the plasmid with msbB(Δ) bla sacB was to be introduced. Since the Salmonella strain contained a second antibiotic resistance marker (e.g., streptomycin resistance), the recombinant Salmonella clones were then selected for dual resistance to ampicillin and streptomycin. To test for resolution of an individual clone, dilutions of each clone were plated on LB lacking sucrose, or LB containing 5% sucrose. Only those strains that underwent deletion or alteration of the sacB gene survive on sucrose. Comparison of the number of clones on sucrose$^{(+)}$ or sucrose$^{(-)}$ plates, indicates the fraction of bacterial cells that underwent resolution. Sucrose resistant colonies were then further tested for sensitivity to ampicillin and tetracycline. Tet$^s$ and amp$^s$ indicated excision of the sacB and bla genes during cross-over with the partial msbB gene region. PCR was then used to confirm the msbB isoform present in the tet$^s$ amp$^s$ clones.

Pre-selection Protocol for the sucrose system

A variation in the normal sucrase protocol allowed for the screening of increased numbers of colonies, by pre-selecting colonies that retain the sacB gene. This pre-selection method eliminated the need for examination and comparison of sucrose$^{(+)}$ vs. sucrose$^{(-)}$ from a large number of colonies. After the conjugation procedure described above, the colonies (impure at this stage) were gridded directly to LB plates containing 5% sucrose and grown at 30° C. The resulting impure colonies, which continued to grow, gave rise to survivors on sucrose. Of the sucrose resistant colonies, those which displayed a phenotypic variation of "fuzzy edges" were then subjected to dilution and plated on sucrose (+) or sucrose (−) plates. Colonies were then tested for sensitivity to tetracycline and ampicillin as above, and the msbB isoform was confirmed by PCR. This improved method was used to generate strains for P22 phage transduction of msbB(Δ) bla sacb chromosomal element. These strains were then used to generate the YS1456 and YS1646 stains, which represent preferred embodiments of the novel msbB mutations of the present invention (see FIGS. 15 and 16).

7.3 DISRUPTION OF SALMONELLA msbB REDUCES TNFα INDUCTION

7.3.1 TNFα INDUCTION IN MICE

WT 14028 and the msbB$^-$ clone YS8211, were first grown to saturation in LB media at 37° C. with shaking at 225 rpm. A 1:100 dilution of these bacterial strains were then transferred to fresh LB and grown to an $OD_{600}$=1.0 at 37° C. with shaking at 225 rpm. The bacteria were diluted in phosphate buffered saline and 1.0×10$^8$ c.f.u. (about 5×10$^9$ c.f.u./kg) were injected into the tail vein of Balb/C mice (n=4/strain), with PBS as a negative control. After 1.5 hours, serum was harvested in triplicate samples by cardiac puncture, centrifuged to remove the cellular content, and analyzed for TNFα using a Biosource International Cytoscreen ELISA plate, which was read on a Molecular Devices Emax microplate reader.

Results are presented in FIG. 4 and expressed as a percent of the level of TNFα induced by wild type Salmonella.

As demonstrated in FIG. 4, YS8211 induced TNFα significantly less than WT 14028. Thus, as shown in FIG. 4, the msbB$^-$ strain induced TNFα about 33% (i.e., 3 times less) of the wild type msbB$^-$ strain.

7.3.2 TNFα INDUCTION IN PIGS

An msbB$^-$ strain of Salmonella, YS8212, and WT 14028, were first grown to saturation in LB media at 37° C. with shaking at 225 rpm. A 1:100 dilution of these bacterial strains were then transferred to fresh LB and grown to an $OD_{600}$=0.8 at 37° C. with 225 rpm. The bacteria were washed in phosphate buffered saline and 1.0×10$^9$ c.f.u. (about 1×10$^8$ c.f.u./kg) were injected into the ear vein of Sinclair swine (n=6/strain). After 1.5 and 6.0 hours, serum was harvested, centrifuged to remove the cellular content, and frozen for later analysis. Analysis for TNFα utilized a Genzyme Predicta ELISA plate, which was read using a Gilson spectrophotometer.

Results are presented in FIG. 5 and are expressed as picograms of TNFα/ml serum.

As demonstrated in FIG. 5, at 90 minutes the level of TNFα induced by the msbB$^-$ strain was significantly lower than that induced by the Salmonella WT 14028.

7.3.3 SALMONELLA LPS-INDUCED RESPIRATION IN PIGS

Lipopolysaccharide (LPS) from Salmonella WT 14028 and the msbB$^-$ clone, YS8212 was prepared using the procedure described by Galanos et al. (1969 Eur. J. Biochem. 9: 245–249). Briefly, LPS was extracted from bacteria which had been grown to $OD_{600}$ of 1.0. The bacteria were pelleted by centrifugation, washed twice with distilled water and frozen at −20° C. LPS was purified by extraction with a mixture of 18.3 ml H2O:15 ml phenol in a shaking water bath for 1 hr at 70° C. The mixture was cooled on ice, centrifuged at 20,000×g for 15 min, and the aqueous phase was removed. LPS was precipitated from the aqueous phase by addition of NaCl to 0.05 M and 2 volumes ethanol and incubation on ice, followed by centrifugation of 2000×g for 10 min. The precipitation was repeated after redissolving the pellet in 0.05 M NaCl, and the pellet lyophilized. The LPS was dissolved in sterile distilled water, and either 5 μg/kg or 500 μg/kg LPS was injected into the ear vein of Sinclair swine which had been anesthetized with Isoflurane. After 1.5 and 6.0 hours, respiration rate was determined and recorded.

Results are presented in FIG. 6 and are expressed as a percentage of respiration at time zero ($t_0$).

As demonstrated in FIG. 6, respiration was significantly higher in the pigs administered wild type LPS as compared to those administered the LPS from the msbB$^-$ strain. Thus, disruption of the msbB gene in Salmonella, produces a modification in lipid A which results in reduced ability to increase respiration.

7.3.4 TNFα INDUCTION IN HUMAN MONOCYTES

Human monocytes were prepared from peripheral blood by centrifugation through Isolymph (Pharmacia) and allowed to adhere to 24 well plates containing RPMI 1640. Salmonella WT 14028 and several of the msbB$^-$ 14028 strains (YS8211, YS8212, YS8658, and YS1170) were first grown to saturation in LB media at 37° C. with shaking at 225 rpm. A 1:100 dilution of these bacterial strains was then transferred to fresh LB and grown to an $OD_{600}$=0.8 at 37° C. with 225 rpm. The bacteria were added to the cell culture wells and the culture medium was harvested after 2.0 hours, centrifuged to remove the cellular content, and analyzed for TNFα using a Genzyme Predicta ELISA plate, which was read using a Gilson spectrophotometer.

The data are presented in FIG. 7 and expressed as picograms of TNFα/ml serum.

As demonstrated in FIG. 7, the msbB$^-$ strains induced TNFα significantly less than did the wild type strain.

7.3.5 msbB$^-$ SALMONELLA LPS TNFα INDUCTION IN HUMAN MONOCYTES

Human monocytes were prepared from peripheral blood by centrifugation through Isolymph (Pharmacia) and allowed to adhere to 24 well plates containing RPMI 1640. Lipopolysaccharide (LPS) of wild type and of a number of msbB$^-$ mutant Salmonella, (i.e., YS8211, YS8212, YS8658 and YS1170) was prepared using the procedure described by Galanos et al. (1969 Eur. J. Biochem. 9: 245–249) (see Section 7.3.3 for a brief description). The LPS was dissolved in sterile distilled water, and quantities ranging from 0.001 to 100 ng/ml LPS were added to the cell culture wells. After 15 hours the culture medium was harvested, centrifuged to remove the cellular content, and analyzed for TNFα using a Genzyme Predicta ELISA plate, which was read using a Gilson spectrophotometer.

The data are presented in FIG. 8 and are expressed as picograms of TNFα/ml serum.

As demonstrated in FIG. 8, LPS purified from the msbB$^-$ strains induced TNFα significantly less than did the LPS from the wild type strain.

7.4 DISRUPTION OF SALMONELLA msbB REDUCES VIRULENCE

7.4.1 IN MICE

A culture of wild type Salmonella 14028 and one of its msbB⁻ Salmonella clones, YS862, were grown in LB medium lacking sodium chloride at 37° C. with shaking at 250 rpm until the cultures reached an $OD_{600}$ of 0.8. The bacteria were diluted into phosphate buffered saline (PBS) at a ratio of 1:10 and the equivalent of $2 \times 10^7$ c.f.u. were injected i.p. into C57BL/6 mice bearing B16F10 melanomas. Survival was determined daily, or at two to four day intervals.

Results are presented in FIG. 9A and are expressed as percent survival.

As shown in FIG. 9A, WT 14028 killed all the mice in 4 days, whereas the msbB⁻ mutant spared 90% of the mice past 20 days, demonstrating a significant reduction in virulence by the msbB⁻ mutant.

7.4.2 IN PIGS

A culture of WT 14028 and one of its msbB⁻ Salmonella clones, YS8212, were grown in LB medium lacking sodium chloride at 37° C. with shaking of 250 RPM until the cultures reached an $OD_{600}$ of 0.8. The bacteria were washed in phosphate buffered saline and $1.0 \times 10^9$ were injected into the ear vein of Sinclair swine (n=4/strain). Survival was determined daily, or at two to four day intervals.

Results are presented in FIG. 9B and are expressed as percent survival.

As shown in FIG. 9B, WT 14028 killed all the swine in 3 days, whereas the msbB⁻ mutant spared 100% of the mice past 20 days, demonstrating a significant reduction in virulence.

7.5 TUMOR TARGETING OF msbB⁻ CLONES

Salmonella WT 14028 with the msbB⁻ modification, were assayed to determine if they possessed tumor targeting ability using the B16F10 melanoma subcutaneous animal model. The msbB⁻ clone, YS8211, was grown in LB media lacking sodium chloride at 37° C. with shaking at 250 rpm to an $OD_{600}$ of 0.8. An aliquot of $2.0 \times 10^6$ c.f.u. was injected i.v. into C57BL/6 mice which had been implanted with $2 \times 10^5$ B16 melanoma cells days prior to the bacterial infection. At two days and five days post bacterial infection, mice were sacrificed and tumors and livers assayed for the presence of the bacteria by homogenization and plating of serial dilutions.

Results are presented in FIG. 10 and are expressed as c.f.u. bacteria/g tissue. As demonstrated in FIG. 10, a positive ratio of tumor to liver (700:1) was found at 2 days, and increased to a positive ratio of 2000:1 at 5 days. Thus, the msbB⁻ mutant maintained the ability to target to a solid cancer tumor.

7.6 USE OF SALMONELLA WITH DISRUPTED msbB FOR ANTI-TUMOR ACTIVITY IN VIVO

Salmonella typhimurium 14028 msbB⁻ clones YS8211, YS8212, YS7216, and YS1629 and WT 14028 (control) were grown in LB media lacking sodium chloride at 37° C. with shaking at 250 rpm to an $OD_{600}$ of 0.8. An aliquot of $2.0 \times 10^6$ c.f.u. was injected i.p. into C57BL/6 mice which had been implanted with $2 \times 10^5$ B16 melanoma cells 8 days prior to the bacterial infection. Tumor volume was monitored over time.

Results are presented in FIG. 11. Two of the strains, YS8211 and YS1629, showed significant tumor retardation, i.e., tumor growth inhibition.

7.7 INCREASED SENSITIVITY TO CHELATING AGENTS

In order to assess the sensitivity of bacterial strains to chelating agents, bacteria with or without the msbB mutation were grown in the presence or absence of 1 mM EDTA or 10 mM sodium citrate in Luria Broth (LB) lacking sodium chloride. An overnight culture of each of the bacterial strains was diluted 1 to 100 in fresh media, and grown at 37° C. with shaking at 250 rpm. The effect on growth was determined by spectrophotometric readings at an $OD_{600}$.

WT 14028 and msbB⁻ clone YS8211 were grown in the presence or absence of 1 mM EDTA (FIG. 12A). EDTA did not inhibit the growth of WT 14028. In contrast, the msbB⁻ clone showed near complete cessation of growth after 3 hours in the presence of EDTA.

WT 14028 and msbB⁻ clone YS862 were grown in the presence and absence of 10 mM sodium citrate (FIG. 12B). The msbB⁺ WT 14028 strain showed little inhibition by sodium citrate compared to the msbB⁻ strain which showed near complete cessation of growth after 3 hours in the presence of sodium citrate.

Thus, the msbB⁻ Salmonella mutants exhibited sensitivity to chelating agents which promote eradication of the bacteria, a characteristic which is similar to an antibiotic effect. It is envisioned that such a characteristic would be advantageous for use of msbB⁻ Salmonella mutants for in vivo therapy.

In order to further assess the sensitivity of Salmonella strains to chelating agents, the hyperinvasive pur strain YS72, its msbB⁻ strain, YS7216, and a derivative of YS7216, YS1629, were grown in the presence of increasing concentrations of EDTA. A fresh culture of YS72, its msbB⁻ strain YS7216 and its faster-growing derivative YS1629 were diluted 1 to 100 in fresh, zero salt LB media containing 0, 0.25, 0.5, 1.0 or 2.0 mM EDTA and grown at 37° C. with 225 RPM for 4 hours, and c.f.u. was determined by plating serial dilutions onto LB plates (Table I). Greater than 99% inhibition was achieved for the msbB⁻ strain YS7216 at concentrations of EDTA greater than 0.25 mM and its derivative YS1629 was inhibited greater than 90% at 0.5 mM and greater than 99% at 2.0 mM. In contrast, although the YS72 clone exhibited some sensitivity to EDTA it was not inhibited at the 90% level even at 2.0 mM.

TABLE I

| Strain | c.f.u. no EDTA | c.f.u. + EDTA {% inhibition} | | | |
|---|---|---|---|---|---|
| | | [0.25 mM] | [0.5 mM] | [1.0 mM] | [2.0 mM] |
| YS72 | $3.0 \times 10^9$ | $2.4 \times 10^9$ {20%} | $1.5 \times 10^9$ {50%} | $7.3 \times 10^8$ {75%} | $4.8 \times 10^8$ {84%} |
| YS7216 | $6.3 \times 10^8$ | $2.1 \times 10^6$ {99.6%} | $1.1 \times 10^6$ {99.8%} | $3.2 \times 10^6$ {99.4%} | $4.3 \times 10^6$ {99.3%} |
| YS1629 | $1.3 \times 10^9$ | $6.0 \times 10^8$ {54%} | $1.0 \times 10^8$ {92%} | $2.9 \times 10^7$ {97%} | $7.5 \times 10^6$ {99.4%} |

7.8 BACTERIAL SURVIVAL WITHIN MACROPHAGES

In order to determine the sensitivity of msbB⁻ Salmonella to macrophages, two types of macrophages were used: (A) bone marrow-derived macrophages obtained from the femurs and tibias of C57BL/6 mice, which were allowed to replicate by addition of supernatant from the LADMAC cell line which secretes macrophage colony stimulating factor (Sklar et al., 1985. J. Cell Physiol. 125:403–412) and (B) J774 cells (a murine macrophage cell line) obtained from America Type Culture Collection (ATCC). Salmonella strains used were WT 14028 and its msbB⁻ derivatives YS8211 and YS1170. Bacteria were grown to late log phase $OD_{600}=0.8$ and $1×10^6$ were allowed to infect a confluent layer of mammalian cells within a 24 well dish for 30 min, after which the extracellular bacteria were removed by washing with culture medium and the addition of 50 µg/ml gentamicin (Elsinghorst, 1994, Methods Enzymol. 236:405–420). Bacteria were counted by plating serial dilutions of the cell layer removed using 0.01% deoxycholate, and expressed as the percent initial c.f.u. over time.

The results are presented in FIG. 13 and expressed as percent c.f.u. per time. The msbB⁻ strain shows significantly less survival in macrophages.

7.9 LD50 OF msbB DERIVATIVES

Spontaneous derivatives of msbB⁻ strains YS8211 and YS7216 were selected from in vitro culture on non-modified LB medium based upon enhanced growth characteristics. These bacterial strains were grown to $OD_{600}$ of 0.8 and c.f.u. ranging from $1×10^2$ to $1×10^8$ were injected i.v. into the tail vein of C57BL/6 mice. Acute lethality was determined at 3 days, and the $LD_{50}$ determined as described by Welkos and O'Brien (Methods in Enzymology 235:29–39, 1994). The results are presented in Table II. Thus, although all the msbB⁻ strains have a reduced ability to induce TNFα (See Section 7.3.5), the results demonstrate that strain YS1170 is significantly less attenuated than other msbB⁻ strains and therefore not all msbB⁻ strains are useful for providing both reduced TNFα induction and reduced virulence.

TABLE II

| Strain | $LD_{50}$ |
|---|---|
| WT 14028 | $1 × 10^3$ |
| YS8211 | $4 × 10^6$ |
| YS8212 | $3.9 × 10^7$ |
| YS1629 | $1 × 10^7$ |
| YS1170 | $1 × 10^6$ |

8. msbB MUTATION IN COMBINATION WITH A BIOSYNTHETIC PATHWAY MUTATION

In order to assess compatibility with auxotrophic mutations, as measured by retention of the ability to target and replicate within tumors, combinations of the msbB mutation with auxotrophic mutations were generated. msbB⁺ strains were grown in LB broth or LB plates containing 1.5% agar at 37° C. msbB strains were grown in modified LB containing 10 g tryptone, 5 g yeast extract, 2 ml 1N CaCl₂ and 2 ml 1N MgSO₄ per liter, adjusted to pH 7 using 1N NaOH. For transducing msbB1::tet, LB lacking NaCl was used, with 4 mg/l tetracycline. Liquid cultures were shaken at 225 rpm. The msbB1::tet was transduced to auxotrophic strains to generate YS1604 (msbB⁻, pur⁻, hyperinvasive), YS7232 (msbB⁻, purI⁻, hyperinvasive), YS7244 (msbB⁻, purI⁻, aroA⁻ hyperinvasive), YS1482 (msbB⁻, purI⁻, purA⁻). For tumor targeting experiments, cells were diluted 1:100 into LB, grown to $OD_{600}=0.8$ to 1.0, washed in phosphate buffered saline (PBS), resuspended in PBS, and $2×10^6$ were injected into the tail vein of C57BL/6 mice. At day 7, tumors were excised, weighed, homogenized, and c.f.u. determined by plating serial dilutions onto modified LB described above.

Results are presented in Table III and are expressed as c.f.u. per gram tumor tissue. Some of the strains, YS8211, YS1604, and YS7232 show high levels of c.f.u. within the tumors, whereas YS7244 and YS1482 are approximately 500 to 5000 times less.

TABLE III

| Strain | genetic marker | c.f.u./gram tumor tissue |
|---|---|---|
| YS8211 | msbB⁻ | $3 × 10^9$ |
| YS1604 | msbB⁻, pur⁻, hyperinvasive | $9 × 10^9$ |
| YS7232 | msbB⁻, purI⁻, hyperinvasive | $9 × 10^9$ |
| YS7244 | msbB⁻, purI⁻, aroA⁻ hyperinvasive | $5 × 10^5$ |
| YS1482 | msbB⁻, purI⁻, purA⁻ | $6 × 10^6$ |

8.1 GENERATION OF THE Y81456 STRAIN CONTAINING DELETIONS IN msbB AND purI

The generation of Salmonella strain YS1456 from the wild type *Salmonella typhimurium* is outlined in FIG. 15. The wild type *Salmonella typhimurium* was transduced with purI 1757::Tn10 which conferred tetracycline-resistance, resulting in strain YS1451.

Strain YS1451 was then subjected to a Bochner selection to render the strain tet sensitive and introduce tet$^s$ gene and introduce a purI deletion (Bochner et al. 1980, J. Bacteriol. 143:926–933), yielding the strain YS1452. Strain YS1452 was tet$^s$ and purI⁻. Strain 1452 was then transduced with msbB1::tet via bacteriophage P22, using strain YS8211 (msbB::tet) as the donor. The resulting strain, YS1453, was initially sensitive to 10 mM ethylene glycol bis((b-aminoethyl ether)-N,N,N ,N'-tetraacetic acid (EGTA), spontaneously reverted to a EGTA-resistant phenotype. One such revertant, denoted YS1454, was selected by plating YS1453 on EGTA (2 mM in Luria agar).

Strain YS1454 was then transduced with the msbB2(Δ) bla sacB chromosomal element, selecting for ampicillin resistance. This transduction process brought in a second version of the disrupted msbB gene, denoted msbB2(Δ) as well as the bla and sacB genes. The bla gene is responsible for the transcription of the enzyme β-lactamase, which metabolizes ampicillin, and was used to select for ampicillin resistant transductants. The sacB gene is responsible for the conversion of sucrose into a toxic chemical, levan, that is lethal to the host cells, and was subsequently used to select for recombinants which lose or have mutations in sacB (see Section 7.2.1 for improved pre-selection methods with sucrose). The presence of the bla and sacB genes allowed the selection of the amp$^r$ and suc$^s$ strain (denoted as strain YS1455), which contained both the msbB1::tet and msbB2 (Δ) genes.

Strain YS1455 was then plated on Luria Bertani (LB) sucrose to select a suc$^r$ amp$^s$ tet$^s$ derivative to remove msbB1::tet and restore antibiotic sensitivity. The derivative was denoted as strain YS1456.

In summary YS1456 has deletion mutations in purI and msbB. It is also tet$^s$ amp$^s$ and EGTA$^r$.

8.2 GENERATION OF THE YS1646 STRAIN CONTAINING DELETIONS IN msbB and purI

The generation of Salmonella strain YS1646 from the wild type *Salmonella typhimurium* (wild type strain ATCC 14028) is outlined in FIG. 16. The wild type *Salmonella* typhimurium was mutagenized with nitrosoguanidine and ultraviolet (UV) light and selected for hyperinvasiveness in melanoma cells. The resistant strain, denoted YS72, were confirmed to possess tumor-hyperinvasiveness pur$^-$ and xyl$^-$ properties (Pawelek et al., 1997, Caner Res 57: 4537–4544).

To replace the chromosomal purI gene in strain YS72 with a purI deletion, strain YS72 was transduced with the purI 1757::Tn10 gene, which conferred tetracycline-resistance. The donor for the purI 1757::Tn10 gene was Salmonella strain TT11 (purI 1757::Tn10). The donor strain was originally obtained from the Salmonella Genetic Stock Center (Dept. of Biological Science, Univ. Calgary, Calgary, Alberta, Canada T2N 1N4). Transduction was performed using bacteriophage P22 (mutant HT105/1 int-201). The transductant, denoted YS1641, was isolated following selection on tetracycline.

Strain YS1641 was then subjected to a Bochner selection to remove the tet gene and introduce a purI gene deletion (Bochner et al., 1980, J. Bacteriol. 143:926–933), yielding strain YS1642. Strain YS1642 was tet$^s$ and purI$^-$. The selection of a tet$^-$-deleted strain allowed further genetic modification (e.g., msbB gene disruption, see next paragraph) using tet gene transduction. Strain YS1642 has a tight purine requirement due to purI($\Delta$), and has been shown to revert to purI$^+$ at a frequency of less than 1 in $10^{10}$ cells.

Strain YS1642 was then transduced with msbB1::tet via bacteriophage P22, using strain YS8211 (msbB::tet) as the donor. The DNA sequence for the msbB gene is shown in FIG. 1. The tet gene in the msbB1::tet gene confers resistance to 5 mg/L of tetracycline. The resulting strain thus obtained was YS1643.

Strain YS1643 was initially sensitive to 10 mM ethylene glycol bis((b-aminoethyl ether)-N,N,N',N'-tetraacetic acid (EGTA), spontaneously reverted to a EGTA-resistant phenotype. One such revertant, denoted YS1644, was selected by plating YS1643 on EGTA (2 mM in Luria agar).

Strain YS1644 was then transduced with the msbB2($\Delta$) bla sacB chromosomal element. This transduction process brought in a second version of the disrupted msbB gene, denoted as msbB2($\Delta$) as well as the bla and sacB genes. The bla gene is responsible for the transcription of the enzyme β-lactamase, which metabolizes ampicillin, and was subsequently used to select transductants. The sacB gene is responsible for the conversion of sucrose into a toxic chemical, levan, that is lethal to the host cells, and was used to select for recombinants. The presence of the bla and sacB genes allowed the selection of the amp$^r$ and suc$^s$ strain (denoted as strain YS1645), which contained both the msbB1::tet and msbB2($\Delta$) genes.

Strain YS1645 was plated on Luria-Bertani (LB) sucrose to select a suc$^r$ amps tet$^s$ derivative to remove the msbB::tet gene and restore antibiotic sensitivity (i.e., a derivative with deletion of msbB1::tet bla sacB). This derivative was denoted as strain YS1646.

In summary YS1646 has deletion mutations in purI, and msbB. It is also tet$^s$, amp$^s$, and EGTA$^r$.

8.3 INHIBITION OF TUMOR GROWTH WITH YS1646 STRAIN

Intravenous (IV) administration of YS1646, an attenuated strain of *Salmonella typhimurium*, resulted in selective replication within tumors, and concomitant inhibition of tumor growth (see FIG. 17 and Table IV).

In all instances, a staged tumor model was used in which tumors were allowed to become established following tumor cell inoculation and prior to YS1646 administration. As a result of the ability of YS1646 to replicate within the tumor, a shallow dose-response relationship over the effective dose range was determined whereby the extent of tumor inhibition, exerted by low doses of YS1646, approached the level of tumor inhibition achieved at higher doses. This suggested that, even at low doses, significant clinical efficacy could be achieved as long as the bacteria reached the tumor and accumulated within the tumor. Doses below $1 \times 10^2$ cfu/mouse gave inconsistent results, possibly due to competition between the ability of YS1646 to reach and colonize the tumor vs. the ability of the animals to clear YS1646.

The efficacy of YS1646 was evaluated in mice previously implanted with B16-F10 melanoma. In this study a single IV dose of YS1646 at $10^4$, $10^5$ or $10^6$ cfu/mouse significantly reduced tumor size when compared to control treatment, and the degree of tumor size reduction was dose-related. The efficacy observed with the highest dose of YS1646 was superior to that with the positive control, CYTOXAN™ (also known as cyclophosamide), whereas the efficacy with the mid-dose of YS1646 was equivalent to that with, CYTOXAN™. It is important to note that the efficacy induced by YS1646 was induced by a single IV dose, whereas that induced by CYTOXAN™ was multiple IV doses (given weekly, for 3 weeks). The ability of YS1646 to inhibit tumor growth, as a function of dose, was examined over an administered dose range of $1 \times 10^4$ to $1 \times 10^6$ cfu/mouse. Each dosage group was comprised of 10 tumor-bearing animals, which were randomized prior to bacteria administration. Mice were administered bacteria on Day 7, and tumor volumes were measured on Days 10, 13, 17, 20, and 24. For comparison, CYTOXAN™ (cyclophosphamide) was administered once per week at a dose of 200 mg/kg, beginning on Day 7 as well. Mean tumor volumes of each group on Day 24 are presented in Table IV.

TABLE IV

| Inoculum Dose (cfu/mouse) | Mean Tumor Volume (mm$^3$) ± S.D. | T/C | Percent Inhibition |
|---|---|---|---|
| 0 | 4728 ± 804 | — | 0 |
| $10^4$ | 1011 ± 375 | 0.214 | 78 |
| $10^5$ | 560 ± 176 | 0.118 | 88 |
| $10^6$ | 279 ± 91 | 0.059 | 94 |

The differences observed between individual groups were deemed significant when analyzed either by the Wilcoxon signed rank test analysis, or by a two-tailed t-test. As indicated in Table IV, increasing tumor inhibition was observed with increasing dose of YS1646. All doses were found to give significant antitumor activity (T/C of less than an equal to 42%), as defined by the Drug Evaluation Branch of the Division of Cancer Treatment, National Cancer Institute (Bethesda, Md.) (Vendetti, J. M., Preclinical drug evaluation: rationale and methods, Semin. Oncol. 8:349–361; 1981), and doses of $1 \times 10^5$ cfu/mouse gave results equivalent to or better than cyclophosphamide. A linear correlation between YS1646 dose and tumor inhibition was not observed due to the ability of YS1646 to replicate preferentially within the tumor, which led to greater than expected potency at lower doses. Intravenous adminstration of YS1646, an attentuated strain of *Salmonella typhimurium*, resulted in selective replication within tumors, and concomitant inhibition of tumor growth. Between inoculum doses of $1 \times 10^4$ to $1 \times 10^6$ cfu/mouse, a dose-response for inhibition of tumor growth was obtained, ranging from 78% to 94% inhibition of tumor growth. At the two highest inoculum doses, the level of tumor growth inhibition was comparable to or better than that achieved by optimal treatment with cyclophosphamide.

8.4 VIRULENCE

At a dose of 1×10⁶ cfu/mouse, YS1646 does not cause lethality, in contrast to the parental wide type strain ATCC 14028, which causes 100% mortality at a dose of 1×10² cfu/mouse. This indicates that YS1646 is greater than 10,000-fold less virulent than the parental wild type strain. The antitumor efficacy was observed at doses of 10⁴ to 10⁶ cfu/mouse, whereas lethality was not observed until the doses were>10⁶ cfu/mouse. The dose inducing mortality was 1 to 100-fold greater than the dose inducing anti-tumor efficacy (see FIG. 18).

8.5 ANTIBIOTIC SUPPRESSION OF YS1646 INDUCED MORTALITY FOLLOWING LETHAL INFECTION

The ability of ampicillin and ciprofoxacin to suppress infection by YS1646 was evaluated by determining the ability of antibiotics to prevent mortality in C57BL/6 mice inoculated with 5×10⁶ cfu (LD$_{50}$ equivalent).

Groups were divided into the following treatment categories: 1) untreated control, 2) ampicillin-treated, 3) ciprofloxacin-treated, and 4) ciprofloxacin and ampicillin treated. Antibiotic treatment was initiated 3 days following bacteria administration and animals were observed daily for appearance and mortality for 14 days. Results presented herein demonstrate that use of antibiotic was able to supress mortality following lethal bacterial infections (see FIG. 18).

9. DEPOSIT OF MICROORGANISMS

The following microorganisms were deposited with the American Type Culture Collection (ATCC), 10801 University Blvd., Manassas, Va. 20110–2209, on Sep. 9, 1997, and have been assigned the indicated Accession numbers:

| Microorganism | ATCC Accession No. |
|---|---|
| YS8211 | 202026 |
| YS1629 | 202025 |
| YS1170 | 202024 |

The following microorganisms were deposited with the American Type Culture Collection (ATCC), 10801 University Blvd., Manassas, Va. 20110–2209, on Aug. 25, 1998, and have been assigned the indicated Accession numbers:

| Microorganism | ATCC Accession No. |
|---|---|
| YS1646 | 202165 |
| YS1456 | 202164 |

The invention claimed and described herein is not to be limited in scope by the specific embodiments, including but not limited to the deposited microorganism embodiments, herein disclosed since these embodiments are intended as illustrations of several aspects of the invention. Indeed, various modifications of the invention in addition to those shown and described herein will become apparent to those skilled in the art from the foregoing description. Such modifications are also intended to fall within the scope of the appended claims.

A number of references are cited herein, the entire disclosures of which are incorporated herein, in their entirety, by reference.

What is claimed is:

1. A mutant Salmonella sp. comprising a genetically modified msbB gene and one or more genetically modified genes to auxotrophy in a tumor targeting Salmonella which is capable of inhibiting the growth of a solid tumor when administered in vivo, wherein said mutant Salmonella expresses an altered lipid A molecule compared to wild type Salmonella sp., induces TNFα expression at a level less than that induced by a wild type Salmonella sp., and is capable of being grown to saturation in LB media at 37° C.

2. The mutant Salmonella of claim 1 which induces TNFα expression at about 5 percent to about 40 percent of that induced by a wild type Salmonella sp.

3. The mutant Salmonella of claim 1 which induces TNFα expression at about 10 percent to about 35 percent of that induced by a wild type Salmonella sp.

4. The mutant Salmonella of claim 1 in which a chelating agent inhibits growth thereof by about 90 percent compared to the growth of a wild type Salmonella sp.

5. The mutant Salmonella of claim 1 in which a chelating agent inhibits growth thereof by about 99 percent compared to the growth of a wild type Salmonella sp.

6. The mutant Salmonella of claim 1 in which a chelating agent inhibits growth thereof greater than 99 percent compared to the growth of a wild type Salmonella sp.

7. The mutant Salmonella of claim 4, 5, or 6 in which the chelating agent is selected from the group consisting of Ethylenediaminetetraacetic Acid (EDTA), Ethylene Glycol-bis(β-aminoethyl Ether) N, N, N', N',-Tetraacetic Acid (EGTA) and sodium citrate.

8. The mutant Salmonella of claim 1 which survives in macrophages at about 50 percent to about 30 percent of the level of survival of a wild type Salmonella sp.

9. The mutant Salmonella of claim 1 which survives in macrophages at about 30 percent to about 10 percent of the level of survival of a wild type Salmonella sp.

10. The mutant Salmonella of claim 1 which survives in macrophages at about 10 percent to about 1 percent of the level of survival of a wild type Salmonella sp.

11. A pharmaceutical composition comprising an amount of the mutant Salmonella of claim 1 effective to inhibit growth or reduce volume of a solid tumor cancer; and a pharmaceutically acceptable carrier.

12. The mutant Salmonella sp. of claim 1, wherein the genetically modified gene to auxotrophy is a genetically modified purI gene.

13. The mutant Salmonella sp. of claim 12 which is designated YS1646 and having ATCC Accession No. 202165 or is designated YS1456 and having the ATCC Accession No. 202164.

14. The mutant Salmonella sp. of claim 1 in which the genetic modifications are deletion mutations.

15. The mutant Salmonella sp. of claim 1, wherein the genetically modified gene to auxotrophy is a genetically modified AroA gene.

16. The mutant Salmonella sp. of claim 1, wherein the genetically modified gene to auxotrophy is a gene in a biosynthetic pathway selected from the group consisting of isoleucine biosynthesis, valine biosynthesis, phenylalanine biosynthesis, tryptophan biosynthesis, tyrosine biosynthesis and arginine biosynthesis.

17. The mutant Salmonella sp. of claim 1, wherein the genetically modified gene to auxotrophy is a gene in a uracil biosynthesis pathway.

18. The mutant Salmonella sp. of claim 1, wherein the genetically modified gene to auxotrophy is a gene in a purine biosynthesis pathway.

19. The mutant Salmonella of claim 1, which has increased growth sensitivity to a chelating agent compared to the growth of a wild type Salmonella sp.

20. The mutant Salmonella of claim 19 in which the chelating agent is selected from the group consisting of Ethylenediaminetetraacetic Acid (EDTA), Ethylene Glycol-bis(β-aminoethyl Ether) N, N, N', N',-Tetraacetic Acid (EGTA) and sodium citrate.

21. A mutant Salmonella sp. comprising a deletion mutation in an msbB gene and one or more deletion mutations in one or more genes to autotrophy in a tumor targeting Salmonella which replicates at physiological temperatures and is capable of inhibiting the growth of a solid tumor when administered in vivo, wherein said mutant Salmonella expresses an altered lipid A molecule compared to wild type Salmonella sp. and induces TNFα expression at a level less than that induced by a wild type Salmonella sp.

22. A mutant Salmonella sp., wherein said mutant Salmonella is designated YS1646 which has been deposited with the ATCC as Accession No. 202165 or is designated YS1456 which has been deposited with the ATCC as Accession No. 202164.

* * * * *

SEQUENCE LISTING

```
<160> NUMBER OF SEQ ID NOS: 4

<210> SEQ ID NO 1
<211> LENGTH: 2019
<212> TYPE: DNA
<213> ORGANISM: SALMONELLA
<220> FEATURE:
<221> NAME/KEY: CDS
<222> LOCATION: (244)..(1212)

<400> SEQUENCE: 1
gatcaaccag caagccgtta accctctgac agcaaaattg ccgcgcacgg aaggtctgac      60
ggggtcagat cgtcgtgaat acctggcaca ggtgaaagag gttctgccgc aactgcgctt     120
cgattaacaa atgcgctgac agagccggta cgcgatgtgt gccggctttt ttgttttgtg     180
tgagacgcag acgtcgctac actattcaca attccttttc gcgtcagcag accctggaaa     240 agc atg gaa acc aaa aaa aat aat agt gag tat atc cct gaa ttc gaa        288
    Met Glu Thr Lys Lys Asn Asn Ser Glu Tyr Ile Pro Glu Phe Glu
      1               5                  10                  15 aaa tcc ttt cgc tat cca cag tat tgg ggc gcc tgg ttg ggc gcg gcg        336
Lys Ser Phe Arg Tyr Pro Gln Tyr Trp Gly Ala Trp Leu Gly Ala Ala
             20                  25                  30
```

```
gca atg gcg ggg atc gca tta aca ccg gca tca ttc cgc gac cct ttg    384
Ala Met Ala Gly Ile Ala Leu Thr Pro Ala Ser Phe Arg Asp Pro Leu
             35                  40                  45 ctg gcg acg ctg ggg cgt ttt gcc gga cgg ctg ggg aag agt tct cgt    432
Leu Ala Thr Leu Gly Arg Phe Ala Gly Arg Leu Gly Lys Ser Ser Arg
         50                  55                  60 cgc cgg gcg cta att aat ctg tcg ttg tgc ttt ccg cag cgt agc gaa    480
Arg Arg Ala Leu Ile Asn Leu Ser Leu Cys Phe Pro Gln Arg Ser Glu
 65                  70                  75 gct gag cgc gaa gcg att gtc gat gag atg ttc gcc acc gcg cca cag    528
Ala Glu Arg Glu Ala Ile Val Asp Glu Met Phe Ala Thr Ala Pro Gln
 80                  85                  90                  95 gca atg gcg atg atg gct gag ttg gcg atg cgc ggt ccg aaa aaa att    576
Ala Met Ala Met Met Ala Glu Leu Ala Met Arg Gly Pro Lys Lys Ile
                100                 105                 110 caa cag cgt gtt gac tgg gaa ggt ctg gag att atc gag gag atg cgt    624
Gln Gln Arg Val Asp Trp Glu Gly Leu Glu Ile Ile Glu Glu Met Arg
            115                 120                 125 cgt aac gac gaa aaa gtc att ttt ctc gta ccg cat ggc tgg ggc gtc    672
Arg Asn Asp Glu Lys Val Ile Phe Leu Val Pro His Gly Trp Gly Val
        130                 135                 140 gac att cca gcc atg ctg atg gcc tct cag ggg caa aaa atg gcg gcg    720
Asp Ile Pro Ala Met Leu Met Ala Ser Gln Gly Gln Lys Met Ala Ala
    145                 150                 155 atg ttt cat aat cag ggt aat ccg gtt ttt gac tat atc tgg aac aca    768
Met Phe His Asn Gln Gly Asn Pro Val Phe Asp Tyr Ile Trp Asn Thr
160                 165                 170                 175 gtg cgt cgg cgt ttc ggc gga cgt ttg cat gcg cgt aat gac ggg att    816
Val Arg Arg Arg Phe Gly Gly Arg Leu His Ala Arg Asn Asp Gly Ile
                180                 185                 190 aaa ccc ttt att cag tct gtt cgt cag ggc tac tgg ggt tac tac ctg    864
Lys Pro Phe Ile Gln Ser Val Arg Gln Gly Tyr Trp Gly Tyr Tyr Leu
            195                 200                 205 ccg gac cag gat cac ggc ccg gag cat agt gaa ttc gtt gat ttc ttt    912
Pro Asp Gln Asp His Gly Pro Glu His Ser Glu Phe Val Asp Phe Phe
        210                 215                 220 gcg aca tac aaa gcg acg ctg cct gca att ggt cgg ctg atg aaa gtg    960
Ala Thr Tyr Lys Ala Thr Leu Pro Ala Ile Gly Arg Leu Met Lys Val
    225                 230                 235 tgc cgc gca cgc gtg ata ccg ctt ttc ccg gtg tat aat ggt aaa acg   1008
Cys Arg Ala Arg Val Ile Pro Leu Phe Pro Val Tyr Asn Gly Lys Thr
240                 245                 250                 255 cat cgc ctg act atc cag att cgc ccg cca atg gac gat ctg ctc acg   1056
His Arg Leu Thr Ile Gln Ile Arg Pro Pro Met Asp Asp Leu Leu Thr
                260                 265                 270 gct gac gac cac act atc gcc aga cgg atg aac gaa gag gtc gaa att   1104
Ala Asp Asp His Thr Ile Ala Arg Arg Met Asn Glu Glu Val Glu Ile
            275                 280                 285 ttt gtc ggc ccg cat ccg gaa cag tac acc tgg atc ctg aag ctg ctc   1152
Phe Val Gly Pro His Pro Glu Gln Tyr Thr Trp Ile Leu Lys Leu Leu
        290                 295                 300 aaa acc cgc aag cca ggc gag att cag ccg tat aag cgt aaa gat ctt   1200
Lys Thr Arg Lys Pro Gly Glu Ile Gln Pro Tyr Lys Arg Lys Asp Leu
305                 310                 315 tat ccc atc aaa taaataaagc ctctcgtaag agaggcttta tgctgacaaa       1252
Tyr Pro Ile Lys
320 ccctgtacta cctgatgaac aggcgtgggg gagttttact caacggtcaa aatacgcgtg  1312
```

-continued

```
gtattggttg aaccgacggt gctcatgaca tcgccctggg tcacgataac caggtcgccg    1372
gaaaccagat acccttatc gcgcagcaga ttaacagctt catgtgccgc gacaacgcca    1432
tcagccgcgc tatcaaaatg caccggcgtt actccgcgat agagcgcggt caggttcagc    1492
gtgcgttcat ggcgcgacat ggcgaaaatc ggcaggccgg agctgatacg ggaagtcatt    1552
agcgcggtac gaccggattc cgtcatggtg atgatcgcgg taacgccttt cagatggttt    1612
gccgcataca ctgcagacat ggcaatggct tcttcaacgt tgtcgaactg cacgtcgaga    1672
cggtgtttag acacattgat gctggggatt ttttctgcgc ccaggcacac gcgcgccatt    1732
gcggcaacgg tttcagaagg atactgaccg gctgcggttt cggcagacag cataaccgca    1792
tccgtgccat ccaggacggc gttcgccacg tccatcactt ccgcacgggt cggcatcggg    1852
ttggtgatca tcgactccat catttgcgtt gcggtgatga ctgcgcggtt tagctgacgc    1912
gcacggcgaa tcagcgcttt ctggatacca accagctccg gatcgccgat ttcaacgccc    1972
agatcgccac gtgcgaccat cacaacgtca gaggccagaa tgatatc                  2019
```

<210> SEQ ID NO 2
<211> LENGTH: 323
<212> TYPE: PRT
<213> ORGANISM: SALMONELLA

<400> SEQUENCE: 2

```
Met Glu Thr Lys Lys Asn Asn Ser Glu Tyr Ile Pro Glu Phe Glu Lys
 1               5                  10                  15

Ser Phe Arg Tyr Pro Gln Tyr Trp Gly Ala Trp Leu Gly Ala Ala Ala
             20                  25                  30

Met Ala Gly Ile Ala Leu Thr Pro Ala Ser Phe Arg Asp Pro Leu Leu
         35                  40                  45

Ala Thr Leu Gly Arg Phe Ala Gly Arg Leu Gly Lys Ser Ser Arg Arg
     50                  55                  60

Arg Ala Leu Ile Asn Leu Ser Leu Cys Phe Pro Gln Arg Ser Glu Ala
 65                  70                  75                  80

Glu Arg Glu Ala Ile Val Asp Glu Met Phe Ala Thr Ala Pro Gln Ala
                 85                  90                  95

Met Ala Met Met Ala Glu Leu Ala Met Arg Gly Pro Lys Lys Ile Gln
            100                 105                 110

Gln Arg Val Asp Trp Glu Gly Leu Glu Ile Ile Glu Glu Met Arg Arg
        115                 120                 125

Asn Asp Glu Lys Val Ile Phe Leu Val Pro His Gly Trp Gly Val Asp
    130                 135                 140

Ile Pro Ala Met Leu Met Ala Ser Gln Gly Gln Lys Met Ala Ala Met
145                 150                 155                 160

Phe His Asn Gln Gly Asn Pro Val Phe Asp Tyr Ile Trp Asn Thr Val
                165                 170                 175

Arg Arg Arg Phe Gly Gly Arg Leu His Ala Arg Asn Asp Gly Ile Lys
            180                 185                 190

Pro Phe Ile Gln Ser Val Arg Gln Gly Tyr Trp Gly Tyr Tyr Leu Pro
        195                 200                 205

Asp Gln Asp His Gly Pro Glu His Ser Glu Phe Val Asp Phe Phe Ala
    210                 215                 220

Thr Tyr Lys Ala Thr Leu Pro Ala Ile Gly Arg Leu Met Lys Val Cys
225                 230                 235                 240

Arg Ala Arg Val Ile Pro Leu Phe Pro Val Tyr Asn Gly Lys Thr His
                245                 250                 255
```

```
Arg Leu Thr Ile Gln Ile Arg Pro Pro Met Asp Asp Leu Leu Thr Ala
            260                 265                 270

Asp Asp His Thr Ile Ala Arg Arg Met Asn Glu Glu Val Glu Ile Phe
        275                 280                 285

Val Gly Pro His Pro Glu Gln Tyr Thr Trp Ile Leu Lys Leu Leu Lys
    290                 295                 300

Thr Arg Lys Pro Gly Glu Ile Gln Pro Tyr Lys Arg Lys Asp Leu Tyr
305                 310                 315                 320

Pro Ile Lys

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 3
gttgactggg aaggtctgga g                                        21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 4
ctgaccgcgc tctatcgcgg                                          20
```